(12) United States Patent
Proudfoot et al.

(10) Patent No.: US 7,425,324 B2
(45) Date of Patent: Sep. 16, 2008

(54) ANTAGONISTS OF MCP PROTEINS

(75) Inventors: Amanda Proudfoot, Chens sur Leman (FR); Marie Kosco-Vilbois, Minzier (FR); Tracy Handel, Oakland, CA (US)

(73) Assignee: Laboratoires Serono SA, Coinsins, Vaud (CH)

( * ) Notice: Subject to any disclaimer, the term of this patent is extended or adjusted under 35 U.S.C. 154(b) by 3 days.

(21) Appl. No.: 10/510,658

(22) PCT Filed: Apr. 9, 2003

(86) PCT No.: PCT/EP03/50097
§ 371 (c)(1),
(2), (4) Date: May 18, 2005

(87) PCT Pub. No.: WO03/084993
PCT Pub. Date: Oct. 16, 2003

(65) Prior Publication Data
US 2007/0004906 A1    Jan. 4, 2007

Related U.S. Application Data

(60) Provisional application No. 60/371,442, filed on Apr. 10, 2002.

(51) Int. Cl.
*A61K 38/19* (2006.01)
*C12N 5/10* (2006.01)
*C12N 15/19* (2006.01)
*C12N 15/63* (2006.01)

(52) U.S. Cl. ............... 424/85.1; 530/324; 536/23.5; 435/69.5; 435/71.1; 435/325; 435/252.3; 435/320.1

(58) Field of Classification Search ............ None
See application file for complete search history.

(56) References Cited

U.S. PATENT DOCUMENTS 5,094,941 A * 3/1992 Hart ..................... 435/7.9
5,116,964 A * 5/1992 Capon et al. ............ 536/23.5

OTHER PUBLICATIONS

Hemmerich et al (1999), Biochemistry, 38, pp. 13013-13025.*
Mikayama et al. Proc. Natl. Acad. Sci. USA vol. 90, pp. 10056-10060.*
Voet et al. Biochemistry John Wiley & Sons, Inc., pp. 126-128 and 228-234.*
Eck & Wilson in Goodman & Gilman's The Pharmacological Basis of Therapeutics, Ninth Edition, McGraw-Hill New York, 1996.*
Hemmerich, S. et al. "Identification of residues in the monocyte chemotactic protein-1 that contact the MCP-1 receptor, CCR2", *Biochemistry*, Oct. 5, 1999, pp. 13013-13025, vol. 38, No. 40.
Steitz, S. A. et al. "Mapping of MCP-1 functional domains by peptide analysis and site-directed mutagenesis", *FEBS Letters*, Jul. 3, 1998, pp. 158-164, vol. 430, No. 3.
Seet, B. T. et al. "Molecular determinants for CC-chemokine recognition by a poxvirus CC-chemokine inhibitor", *Proceedings of the National Academy of Sciences of the United States*, Jul. 31, 2001, pp. 9008-9013, vol. 98, No, 16.
Mayer, M. R. et al. "Identification of receptor binding and activation determinants in the N-terminal and N-loop regions of the CC chemokine eotaxin", *Journal of Biological Chemistry*, Apr. 27, 2001, pp. 13911-13916, vol. 276, No. 17.
Chakravarty, L. et al. "Lysine 58 and histidine 66 at the C-terminal alpha-helix of monocyte chemoattractant protein-1 are essential for glycosaminoglycan binding", *Journal of Biological Chemistry*, Nov. 6, 1998, pp. 29641-29647, vol. 273, No. 45.
Dawson, J. et al. "Targeting monocyte chemoattractant protein-1 signaling in disease", *Expert Opinion on Therapeutic Targets*, Feb. 2003, pp. 35-48, vol. 7, No. 1.
Proudfoot, A. E. I. et al. "Glycosaminoglycan binding and oligomerization are essential for the in vivo activity of certain chemokines", *PNAS*, Feb. 18, 2003, pp. 1885-1890, vol. 100, No. 4.

* cited by examiner

*Primary Examiner*—Prema Mertz
(74) *Attorney, Agent, or Firm*—Saliwanchik, Lloyd & Saliwanchik

(57) ABSTRACT

Novel antagonists of MCP proteins, in particular of MCP-1 protein, can be obtained by generating MCP mutants whose GAG binding site, located at the N-terminal of MCP proteins, is eliminated following non-conservative substitutions. Compounds prepared in accordance with the present invention can be used in the treatment or prevention of diseases related to an undesirable activity of MCP proteins such, such as inflammatory disease, autoimmune diseases, vascular diseases, and cancer.

28 Claims, 11 Drawing Sheets

```
hMCP-1     1  MKVSAALLCL LLIAATFIPQ GLAQPDAINA PVTCCYNFTN RKISVQRLAS  50
MCP-1WT*   1                        MQPDAINA PVTCCYNFTN RKISVQRLAS  28
MCP-1WT*2A 1                        MQPDAINA PVTCCYNFTN AAISVQRLAS  28 hMCP1      51 YRRITSSKCP KEAVIFKTIV AKEICADPKQ KWVQDSMDHL DKQTQTPKT  99
MCP-1WT*   29 YRRITSSKCP KEAVIFKTIV AKEICADPKQ KWVQDSIDHL DKQTQTPKT  77
MCP-1WT*2A 29 YRRITSSKCP KEAVIFKTIV AKEICADPKQ KWVQDSIDHL DKQTQTPKT  77
```

B)

```
hMCP-1    1 QPDAINAPVT CCYNFTN[RK]I SVQRLASYRR ITSSKCPKEA VIFKTIVAKE  50
hMCP-2    1 QPDSVSIPIT CCFNVIN[RK]I PIQRLESYTR ITNIQCPKEA VIFKTKRGKE  50
hMCP-3    1 QPVGINTSTT CCYRFIN[KK]I PKQRLESYRR TTSSHCPREA VIFKTKLDKE  50
hMCP-4    1 QPDALNVPST CCFTFSS[KK]I SLQRLKSYV- ITTSRCPQKA VIFRTKLGKE  49
Eotaxin   1   GPASVPTT CCFNLAN[RK]I PLQRLESYRR ITSGKCPQKA VIFKTKLAKD  48 hMCP-1   51 ICADPKQKWV QDSMDHLDKQ TQTPKT  76
hMCP-2   51 VCADPKERWV RDSMKHLDQI FQNLKP  76
hMCP-3   51 ICADPTQKWV QDFMKHLDKK TQTPKL  76
hMCP-4   50 ICADPKEKWV QNYMKHLGRK AHTLKT  75
Eotaxin  49 ICADPKKKWV QDSMKYLDQK SPTPKP  74
```

☐ PBS
▲ MCP-1WT* (10 micrograms)
■ MCP-1WT*2A (10 micrograms)
▼ MCP-1WT* (10 micrograms) + MCP-1WT*2A (10 micrograms)
● MCP-1WT* (10 micrograms) + MCP-1WT*2A (1 microgram)
◆ MCP-1WT* (10 micrograms) + MCP-1WT*2A (0.1 microgram)

Figure 8
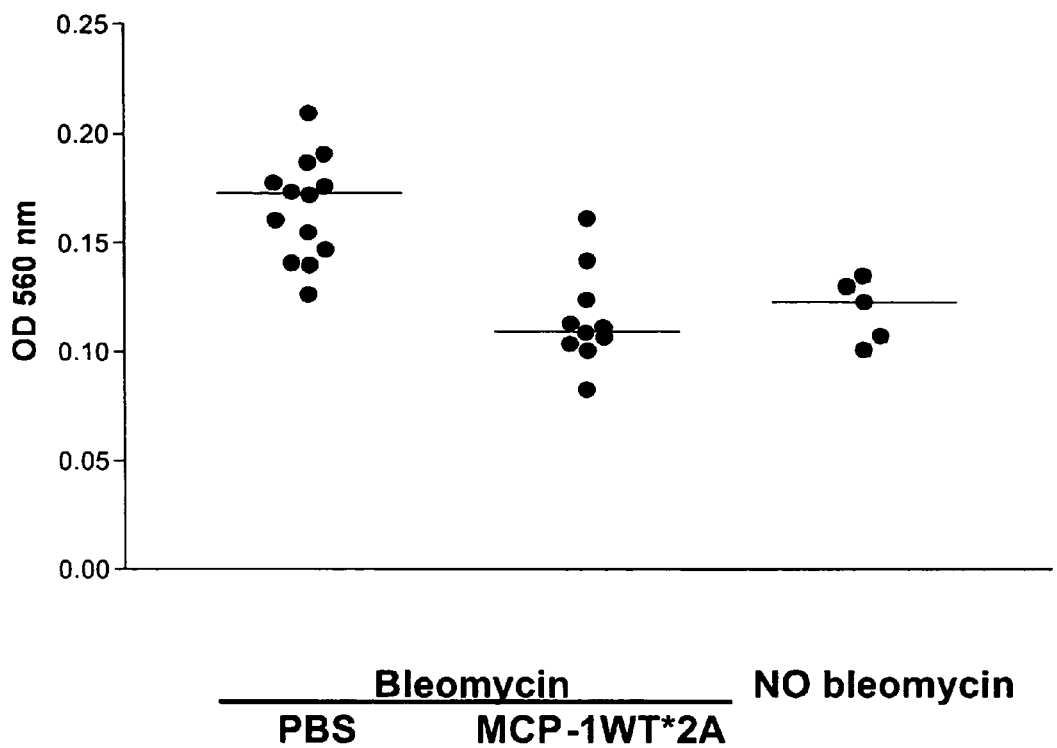
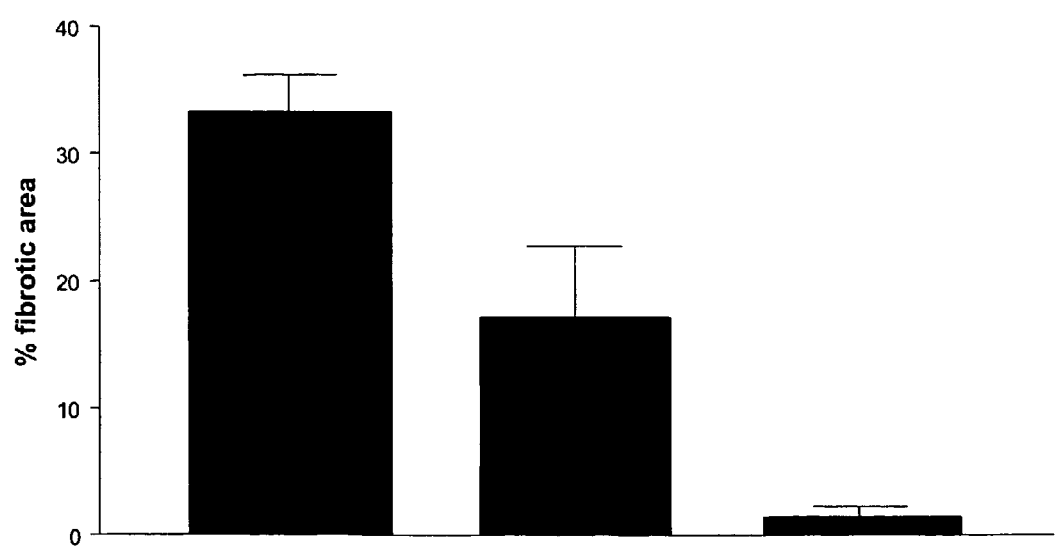

ANTAGONISTS OF MCP PROTEINS

CROSS-REFERENCE TO RELATED APPLICATION

This application is the U.S. national stage application of International Patent Application No. PCT/EP03/50097, filed Apr. 9, 2003, which claims the benefit of U.S. Provisional Patent Application No. 60/371,442, filed Apr. 10, 2002.

FIELD OF THE INVENTION

The present invention is directed to novel antagonists of MCP proteins, and in particular of human MCP-1, which have been generated by appropriately mutagenising MCP proteins.

BACKGROUND OF THE INVENTION

Chemokines are small secreted pro-inflammatory proteins, which mediate directional migration of leukocytes from the blood to the site of injury. Depending on the position of the conserved cysteines characterizing this family of proteins, the chemokine family can be divided structurally in C, C-C, C-X-C and C-$X_3$-C chemokines, to which corresponds a series of membrane receptors (Baggiolini M et al., 1997; Fernandez E J and Lolis E, 2002). Usually chemokines are produced at the site of injury and cause leukocyte migration and activation, playing a fundamental role in inflammatory, immune, homeostatic and angiogenic processes. These molecules, therefore, offer the possibility for therapeutic intervention in diseases associated to such processes, in particular by inhibiting specific chemokines and their receptors at the scope to preventing the excessive recruitment and activation of leukocytes (Baggiolini M, 2001; Loetscher P and Clark-Lewis I, 2001; Godessart N and Kunkel S L, 2001).

Monocyte chemoattractant protein 1 (from now on, MCP-1) is a member of the CC chemokine family also known under various names such as CCL2, Small Inducible Cytokine A2 (SCYA2), Monocyte Chemotactic And Activating Factor (MCAF), Monocyte Secretory Protein Je, Monocyte Chemotactic Factor, and HC11. This chemokine is capable of promoting the recruitment of monocytes and basophils in response to injury and infection signals in various inflammatory diseases, different types of tumors, cardiac allograft, AIDS, and tuberculosis (Gu L et al., 1999).

Structurally and functionally homologous proteins have been identified and called MCP-2 (CCL7), MCP-3 (CCL8), MCP-4 (CCL13), and Eotaxin (CCL11). This subfamily of C-C chemokines is significantly distinct from other C-C chemokines, such as RANTES or MIP-1alpha/beta, and probably coevolved from a common progenitor sequence. They have a similar receptor usage, binding in particular CCR2 (but also for CCR1, CCR3, and CCR5). Therefore, many of the immunological and inflammatory agonistic or antagonistic activities of these C-C chemokines are common (Hughes A L and Yeager M, 1999; Berhkout T A et al., 1997; Luster A D and Rothenberg M E, 1997, Proost P et al., 1996).

The physiological activities associated with MCP-1 have been extensively studied by means of transgenic animals and other animal models, which demonstrate that MCP-1 controls recruitment of monocytes and of other cell types (astrocytes, for example) in many infectious, inflammatory and autoimmune diseases, as well as the expression of cytokines related to T helper responses. Other diseases that appear induced by MCP-1 are vascular disorders (restenosis after coronary intervention, arteriosclerosis, atherosclerosis, ischemia, stroke) and cancer-related angiogenesis (Ikeda Y et al., 2002; Egashira K et al., 2002; Gu L et al., 2000; Salcedo R et al., 2000; Gosling J et al, 1999; Lu B et al, 1998; Rutledge B J et al., 1995).

Since MCP-1 targeting is considered as a possible therapeutic approach for several diseases, different types of MCP-1 antagonists have been described in the literature, obtaining more or less important inhibitory effect on MCP-1-induced pathological activities (Dawson J, 2003). Examples of MCP-1 antagonists are an N-terminal deletion mutant of MCP-1, natural or synthetic, missing the N-terminal amino acids 2 to 10 (Egashira K et al., 2000; Zhang Y and Rollins B J, 1995; McQuibban G A et al., 2002), anti-MCP-1 monoclonal antibodies (Ajuebor M N et al., 1998; Eghtesad M et al., 2001), RNA aptamers (Rhodes A et al., 2001), peptides designed on sequences internal to MCP-1 (Reckless J and Grainger D J, 1999), MCP-1 antagonists peptide mimics (Kaji M et al., 2001), antisense oligonucleotides (WO 94/09128), small molecules (Mirzadegan T et al., 2000), polymer-modified MCP-1 (WO 02/04015), or viral decoy receptors (Alexander J M et al., 2002; Beck C G et al., 2001).

Structurally, MCP proteins present a N-terminal loop and three β-sheets overlaid by a α-helix at the C-terminal end (Handel T M et al., 1996; Lubkowski J, et al., 1997; Blaszczyk J et al., 2000). The literature provides many examples of structure-activity studies (Gong J H and Clark-Lewis 1, 1995; Zhang et al., 1996; Beall C J et al., 1996; Steitz S A et al., 1998; Gu L et al., 1999; Hemmerich S et al., 1999; Seet B T et al., 2001) in which MCP-1 mutants have reduced activity and/or affinity for the receptor or other binding proteins have been obtained by expressing N-terminal truncations (as in many other chemokines), or single mutations at residues 3, 8, 10, 13, 15, 18, 19, 24, 28, 30, 37, 38, and 39 (following the numbering of mature human MCP-1). Similar results have been obtained for Eotaxin (Mayer M R and Stone M J, 2001).

Chemokines interact with proteoglycans (PGs) and glycosaminoglycans (GAGs) a feature common to many cell-signaling soluble molecules (interleukins, growth factors). Proteoglycans are negatively charged proteins that are post-translationally modified by the addition of glycosaminoglycan side chains at serine residues. Clusters of basic residues (mainly Arginines and Lysines) allow proteins to interact with GAGs, which commonly are characterized by the disaccharide repeats such as heparin, chondroitin sulfate, heparan sulfate, dermatan sulfate, and hyaluronic acid). PGs and GAGs can be present on membrane surfaces as well as soluble molecules, probably at the scope to protect this molecule from proteolysis in the extracellular environment. It has been also proposed that GAGs may help the correct presentation of cell signaling molecules to their specific receptor and, eventually, also the modulation of target cell activation. In the case of chemokines, the concentration into immobilized gradients at the site of inflammation and, consequently, the interaction with cell receptors and their activation state seem to be modulated by the specific GAG. The interaction with GAGs and the formation of these gradients have been clearly demonstrated for many chemokines, including MCP-1, measuring the relative affinity. Therefore, it has been suggested that the modulation of such interactions may represent a therapeutic approach in inflammatory disease (Hoogewerf A J et al., 1997; Kuschert G et al., 1999; Ali S et al., 2001; Patel D et al., 2001; WO 02/28419; WO 99/50246).

However, the structural requirements and functional effects of GAG/MCP-1 interactions have been poorly studied. It is known that GAGs can modulate the activity and production of MCP-1 secreted from endothelial cells (Douglas M S et al., 1997). It has been also reported that substitution of Lysine 58 and Histidine 66 with Alanines in the C-terminal of MCP-1, prevents GAG binding without affecting receptor binding, $Ca^{2+}$ influx, or chemotactic activity (Chakravarty L et al, 1998), but there is no disclosure in the prior art of which may be other GAG binding sites of MCP-1, and which in vivo effects can be consequent to their elimination. Even though extensive studies have been performed on some chemokines, it is not possible to anticipate, on the basis of the sequence homology, which residues have to be modified with non-conservative substitutions to impair GAG binding, and which effects can be obtained, since there is a significant structural diversity of GAG binding domains in chemokines (Lortat-Jacob H et al., 2002).

SUMMARY OF THE INVENTION

It has been found that a dibasic site at the N-terminal of human MCP-1 (Arginine 18, Lysine 19) is responsible for the interaction of MCP-1 with GAGs. The elimination of this site by non-conservative substitutions (for example, with Alanines) allows to generate MCP-1 mutants having not only have a reduced tendency to interact with GAG, but a surprising in vivo, dose-related antagonistic activities on MCP-1. Such evidence can be exploited to use mutants of MCP-1, and of other MCP proteins, as antagonists of the corresponding MCP protein. Compounds prepared in accordance with the present invention can be used to inhibit the migration and activation of leukocytes expressing their receptors, thereby providing useful therapeutic compositions for use in the treatment of diseases related to excessive or uncontrolled leukocyte migration, such as inflammation and autoimmune diseases. Other features and advantages of the invention will be apparent from the following detailed description.

DESCRIPTION OF THE FIGURES

FIG. 1: (A) amino acid sequences of human and mutated MCP-1 proteins as expressed and tested in the Examples (mutated amino acids are underlined). The N-terminal methionine in MCP-1WT* and MCP-1WT*2A was removed during purification by aminopeptidase treatment to avoid any interference on the activity of the protein due to this addition al residue. (B) Alignment of the mature forms of human MCP-1 (CCL2; SWISSPROT Acc. No. P13500), MCP-2 (CCL7; SWISSPROT Acc. No. P80075), MCP-3 (CCL8; SWISSPROT Acc. No. P80098), MCP4 (CCL8; SWISSPROT Acc. No. Q99616), and Eotaxin (CCL11, SWISSPROT Acc. No. P51671). The basic residues identified in MCP-1 in the present patent application as being involved in the binding with GAGs (residues 18 and 19) and the conserved corresponding residues in the more homologous human proteins are boxed. Other basic residues conserved amongst all human MCP proteins are underlined.

FIG. 8: graph comparing the fibrosis levels in untreated and bleomycin-treated mice, which were additionally treated with PBS only, or with an intraperitoneal administration of 0.25 mg/kg MCP-1WT*2A. Fibrosis levels were measured either spectroscopically (top) or histologically (bottom) as described in the Examples.

DETAILED DESCRIPTION OF THE INVENTION

Figure 2:
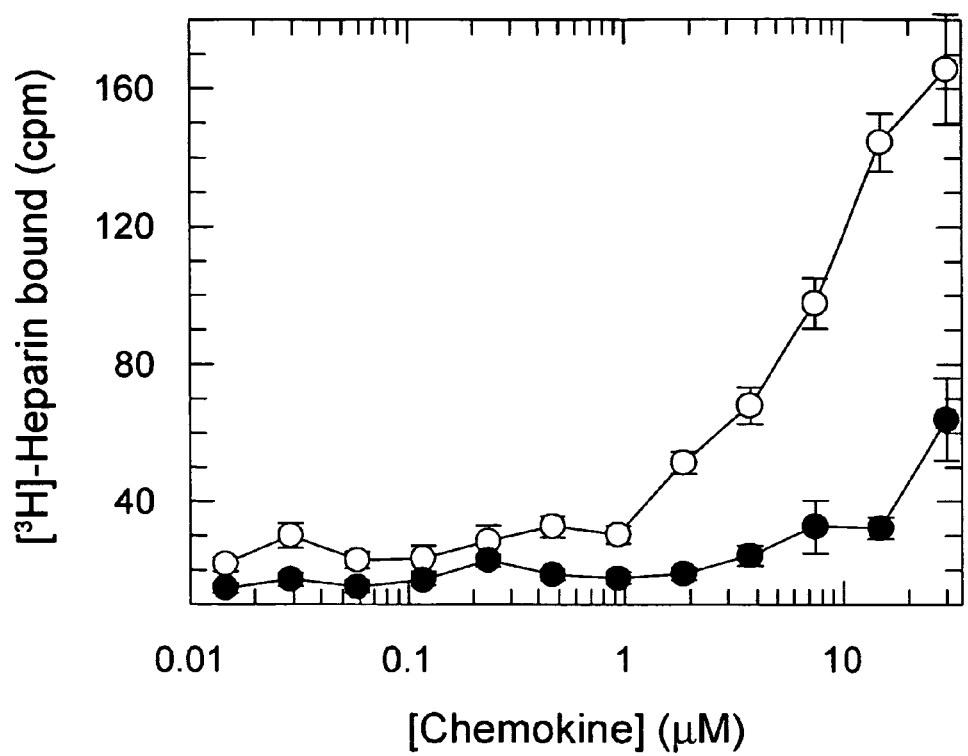
FIG. 2: graph representing the results of the heparin binding assay performed with [$^3$H]-heparin and, as chemokine, either MCP-1WT* (○) or MCP-1WT*2A (●).

In view of the literature mentioned above, there is no indication that a specific dibasic site in the N-terminus of human MCP-1 defines a GAG binding site, and that the non-conservative substitution of the residues in this site leads to molecules having antagonistic activity on MCP-1. Moreover, given the conservation of this dibasic site amongst known MCP proteins, as well as of other residues which are basic and/or known to be involved in GAG binding, it can be inferred that the antagonists of MCP proteins can be obtained by non-conservative substitutions in the residues corresponding to the ones functionally characterized in human MCP-1.

The main object of the present invention is to provide novel antagonists of MCP proteins consisting of mutants of MCP proteins in which the following combinations of residues, numbered on the sequence of human mature MCP-1, are substituted to Alanine, Glycine, Serine, Threonine, Proline, Aspartic acid, Asparagine, Glutamic acid, or Glutamine:

a) 18 and 19;
b) 18 and/or 19, together with 58;
c) 18 and/or 19, together with 66;
d) 18 and/or 19, together with 58 and 66;
e) 18 and/or 19, together with one or more of the following: 24, 44, 49, 75.

The present patent application provides surprising in vivo and in vitro data obtained with a novel recombinant MCP-1 mutant in which Arginine 18 and Lysine 19 were substituted with Alanines, which is a particular example of the combinations described above. These results, combined with the knowledge on the sequence and the structure of other highly conserved MCP proteins suggests that this dibasic site can play not only a general role in MCP proteins biological activity, but also can be modified accordingly in these homologous proteins to obtain antagonist molecules.

The basic residues which have to be mutated in a non-conservative manner in MCP proteins to obtain molecules having antagonistic properties are essentially both residues in positions 18 and 19, at least one of the basic residues in position 18 and 19 combined with at least one of the residues already known to be involved in GAG binding, such as 58 and 66 (Chakravarty L et al., 1999), or at least one of the basic residues in position 18 and 19 combined with at least one of the other basic residues which are conserved in all human MCP proteins (FIG. 1B; Berhkout T A et al., 1997). The amino acid replacing the basic residue is preferably a non-polar, small amino acid like Alanine or Glycine, but other amino acids are appropriate, provided that they have a charge and dimension which poorly interfere with the structure of the protein and, at the same time, are incompatible with GAG binding, for example Serine, Threonine, Proline, Aspartic acid, Asparagine, Glutamic acid, or Glutamine.

Therefore the main object of the present invention is to provide mutants of MCP proteins which contain a combination of the mutations defined above, and which act as antagonists of MCP proteins.

The term "antagonist of MCP proteins" means any molecule, which acts as antagonist to the corresponding mature full-length, naturally-occurring (wild-type) MCP protein. MCP-1 antagonists known in the art involves modifications In the sense of the present application, the term MCP proteins include human MCP-1, human MCP-2, human MCP-3, human MCP4, and human Eotaxin (FIG. 1B; the legend indicates the corresponding SWISSPROT accession numbers), as well as any other protein having at least 70%, preferably 80%, and more preferably 90% of homology with human mature MCP-1, MCP-2, MCP-3, MCP-4, or Eotaxin and containing a basic, positively charged amino acid (Arginine, Lysine, or Histidine) in all the positions identified above.

Further objects of the present invention are antagonists of MCP proteins selected from:
 a) active mutants of the above defined mutants of MCP proteins in which one or more amino acid residues have been added, deleted, or substituted without interfering with the antagonistic activity;
 b) peptide mimetics designed on the sequence and/or the structure of polypeptides or peptides of (a);
 c) polypeptides or peptides comprising the amino acid sequence of (a) or (b), and an amino acid sequence belonging to a protein sequence other than the corresponding MCP protein;
 d) active fractions, precursors, salts, or derivatives of (a), (b), or (c).

The antagonistic properties of MCP mutants defined above, and exemplified in the present patent application using MCP-1WT*2A as MCP-1 antagonist, can be maintained, or even potentiated, in the active mutants. This category of molecules includes natural or artificial analogs of said sequence, wherein one or more amino acid residues have been added, deleted, or substituted, provided they display the same biological activity characterized in the present invention at comparable or higher levels, as determined by means known in the art and disclosed in the Examples below.

For example, acceptable substitutions should be directed to residues not involved in GAG binding, like the substitution of Methionine 64 with an Isoleucine shown in the examples (MCP-1WT*2A; SEQ ID NO: 3) to improve purification without altering essential properties of human MCP-1. Another object of the present invention is therefore an MCP-1 antagonists having the sequence corresponding to MCP-1WT*2A (SEQ ID NO: 3). Alternatively, the MCP-1 antagonists, in addition to the substitutions directed to the residues involved to GAG binding, may miss 2 to 10 N-terminal amino acids, as in the known N-terminal deletion mutants of MCP-1 (Egashira K et al., 2000; Zhang Y and Rollins B J, 1995; McQuibban G A et al., 2002), possibly obtaining improved antagonistic properties.

Natural analogs are intended the corresponding sequences of MCP proteins identified in humans or in other organisms, like mouse MCP-1 (SWISSPROT Acc. No. P10148). Artificial analogs are intended peptides prepared by known chemical synthesis and/or by site-directed mutagenesis techniques, or any other known technique suitable thereof, which provide a finite set of substantially corresponding mutated or shortened peptides or polypeptides which can be routinely obtained and tested by one of ordinary skill in the art using the teachings presented in the prior art and in the Examples of the present patent application.

In accordance with the present invention, preferred changes in these active mutants are commonly known as "conservative" or "safe" substitutions, and involve non-basic residues. Conservative amino acid substitutions are those with amino acids having sufficiently similar chemical properties, in order to preserve the structure and the biological function of the molecule. It is clear that insertions and deletions of amino acids may also be made in the above defined sequences without altering their function, particularly if the insertions or deletions only involve a few amino acids, e.g., under ten, and preferably under three, and do not remove or displace amino acids which are critical to the functional conformation of a protein or a peptide.

The literature provide many models on which the selection of conservative amino acids substitutions can be performed on the basis of statistical and physico-chemical studies on the sequence and/or the structure of natural protein (Rogov S I and Nekrasov A N, 2001). Protein design experiments have shown that the use of specific subsets of amino acids can produce foldable and active proteins, helping in the classification of amino acid "synonymous" substitutions which can be more easily accommodated in protein structure, and which can be used to detect functional and structural homologs and paralogs (Murphy L R et al., 2000). The synonymous amino acid groups and more preferred synonymous groups are those defined in Table I.

Active mutants produced by substitutions made on the basis of these teachings, as well as active mutants wherein one or more amino acids were eliminated or added, are amongst the objects of the present invention, that is, novel mutants of MCP proteins having poor GAG binding properties and antagonistic activity on the corresponding MCP protein, comparable to the ones of the initially selected mutants, or even improved if possible.

The above described alternative compounds are intended to comprehend molecules with changes to the sequence of the mutants of MCP proteins defined above which do not affect the basic characteristics disclosed in the present patent application, particularly insofar as its ability as antagonists is concerned. Similar compounds may result from conventional mutagenesis technique of the encoding DNA, from combinatorial technologies at the level of encoding DNA sequence (such as DNA shuffling, phage display/selection), or from computer-aided design studies, followed by the validation for the desired activities as described in the prior art and in the Examples below.

Specific antagonists can be obtained in the form of peptide mimetics (also called peptidomimetics) of the MCP mutants above defined, in which the nature of peptide or polypeptide has been chemically modified at the level of amino acid side chains, of amino acid chirality, and/or of the peptide backbone. These alterations are intended to provide MCP antagonists having similar or improved therapeutic, diagnostic and/or pharmacokinetic properties.

For example, when the peptide is susceptible to cleavage by peptidases following injection into the subject is a problem, replacement of a particularly sensitive peptide bond with a non-cleavable peptide mimetic can provide a peptide more stable and thus more useful as a therapeutic. Similarly, the replacement of an L-amino acid residue is a standard way of rendering the peptide less sensitive to proteolysis, and finally more similar to organic compounds other than peptides. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenyl-methoxycarbonyl, methoxyazelayl, methoxyadipyl, methoxysuberyl, and 2,4-dinitrophenyl. Many other modifications providing increased potency, prolonged activity, easiness of purification, and/or increased half-life are known in the art (WO 02/10195; Villain M et al., 2001). Preferred alternative, "synonymous" groups for amino acids included in peptide mimetics are those defined in Table II.

The techniques for the synthesis and the development of peptide mimetics, as well as non-peptide mimetics, are well known in the art (Sawyer T K, 1997; Hruby V J and Balse P M, 2000; Golebiowski A et al., 2001). Various methodology for incorporating unnatural amino acids into proteins, using both in vitro and in vivo translation systems, to probe and/or improve protein structure and function are also disclosed in the literature (Dougherty D A, 2000). MCP-1 antagonists peptide mimics are known in the literature, without being highly homologous to MCP-1 (Kaji M et al., 2001).

The present patent application discloses as MCP antagonists polypeptides or peptides comprising the amino acid sequence as defined above and an amino acid sequence belonging to a protein sequence other than the corresponding MCP protein. This heterologous latter sequence should provide additional properties without impairing significatively the antagonistic activity, or proving GAG binding properties. Examples of such additional properties are an easier purification procedure, a longer lasting half-life in body fluids, or extracellular localization. This latter feature is of particular importance for defining a specific group of fusion or chimeric proteins included in the above definition since it allows the molecules defined as MCP antagonists in this patent application to be localized in the space where not only where the isolation and purification of these peptides is facilitated, but also where MCP proteins and their receptor naturally interact.

Additional protein sequences which can be used to generate the polypeptide or peptide of (c) are the ones of extracellular domains of membrane-bound protein, immunoglobulin constant region, multimerization domains, extracellular proteins, signal peptide-containing proteins, export signal-containing proteins. The choice of one or more of these sequences to be fused to the mutant of MCP protein is functional to specific use of said agent. As a general procedure, these fusion proteins can be produced by generating nucleic acid segments encoding them, using common genetic engineering techniques, and cloning in replicable vector of viral or plasmid origin which are used to modify a Prokaryotic or Eukaryotic host cell, using episomal or non-/homologously integrated vectors, as well as transformation-, infection-, or transfection-based technologies. These vectors should allow the expression of the fusion protein including the MCP antagonist in the prokaryotic or eukaryotic host cell under the control of their own transcriptional initiation/termination regulatory sequences, which are chosen to be constitutively active or inducible in said cell. A cell line substantially enriched in such cells can be then isolated to provide a stable cell line.

When the additional protein sequence, as in the case of the sequence of extracellular, export signal, or signal-peptide containing proteins, allows the MCP antagonists to be secreted in the extracellular space, the agent can be more easily collected and purified from cultured cells in view of further processing or, alternatively, the cells can be directly used or administered.

The polypeptides and the peptides of the present invention can be in other alternative forms which can be preferred according to the desired method of use and/or production, for example as active fractions, precursors, salts, derivatives, conjugates or complexes.

The term "active" means that such alternative compounds should maintain the functional features of the MCP mutants of the present invention, and should be as well pharmaceutically acceptable and useful.

The term "fraction" refers to any fragment of the polypeptidic chain of the compound itself, alone or in combination with related molecules or residues bound to it, for example residues of sugars or phosphates, or aggregates of the original polypeptide or peptide. Such molecules can result also from other modifications which do not normally alter primary sequence, for example in vivo or in vitro chemical derivativization of peptides (acetylation or carboxylation), those made by modifying the pattern of phosphorylation (introduction of phosphotyrosine, p hosphoserine, or phosphothreonine residues) or glycosylation (by exposing the peptide to enzymes which affect glycosylation e.g., mammalian glycosylating or deglycosylating enzymes) of a peptide during its synthesis and processing or in further processing steps.

The "precursors" are compounds which can be converted into the compounds of present invention by metabolic and enzymatic processing prior or after the administration to the cells or to the body.

The term "salts" herein refers to both salts of carboxyl groups and to acid addition salts of amino groups of the peptides, polypeptides, or analogs thereof, of the present invention. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the peptides and polypeptides of the invention or their analogs.

The term "derivatives" as herein used refers to derivatives which can be prepared from the functional groups present on the lateral chains of the amino acid moieties or on the N-/ or C-terminal groups according to known methods. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

Useful conjugates or complexes of the MCP antagonists of the present invention can be generated, using molecules and methods known in the art of the interaction with receptor or other proteins (radioactive or fluorescent labels, biotin), therapeutic efficacy (cytotoxic agents), or improving the agents in terms of drug delivery efficacy, such as polyethylene glycol and other natural or synthetic polymers (Pillai O and Panchagnula R, 2001).

The compounds of the invention may be prepared by any well known procedure in the art, including recombinant DNA-related technologies described above, and chemical synthesis technologies.

Another object of the invention are the DNA molecules comprising the DNA sequences coding for the MCP mutants of the invention, including nucleotide sequences substantially the same. "Nucleotide sequences substantially the same" includes all other nucleic acid sequences that, by virtue of the degeneracy of the genetic code, also code for the given amino acid sequences.

The invention also includes expression vectors which comprise the above DNAs, host cells transformed with such vectors and a process of preparation of MCP antagonists of the invention, through the culture in appropriate culture media of said transformed cells, and collecting the expressed protein.

The DNA sequence coding for the proteins of the invention can be inserted and ligated into a suitable plasmid. Once formed, the expression vector is introduced into a suitable host cell, which then expresses the vector(s) to yield the desired protein.

Expression of any of the recombinant proteins of the invention as mentioned herein can be effected in eukaryotic cells (e.g. yeasts, insect or mammalian cells) or prokaryotic cells, using the appropriate expression vectors. Any method known in the art can be employed.

For example the DNA molecules coding for the proteins obtained by any of the above methods are inserted into appropriately constructed expression vectors by techniques well known in the art. Double stranded cDNA is linked to plasmid vectors by homopolymeric tailing or by restriction linking involving the use of synthetic DNA linkers or blunt-ended ligation techniques: DNA ligases are used to ligate the DNA molecules, and undesirable joining is avoided by treatment with alkaline phosphatase.

In order to be capable of expressing the desired protein, an expression vector should also comprise specific nucleotide sequences containing transcriptional and translational regulatory information linked to the DNA coding the desired protein in such a way as to permit gene expression and production of the protein. First in order for the gene to be transcribed, it must be preceded by a promoter recognizable by RNA polymerase, to which the polymerase binds and thus initiates the transcription process. There are a variety of such promoters in use, which work with different efficiencies (strong and weak promoters).

For Eukaryotic hosts, different transcriptional and translational regulatory sequences may be employed, depending on the nature of the host. They may be derived form viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for the protein of the invention is inserted into vector(s), having the operably linked transcriptional and translational regulatory signals, which is capable of integrating the desired gene sequences into the host cell.

The cells that have been stably transformed by the introduced DNA can be selected by also introducing one or more markers allowing for selection of host cells containing the expression vector. The marker may also provide for phototrophy to an auxotropic host, biocide resistance, e.g. antibiotics, or heavy metals such as copper, or the like. The selectable marker gene can either be directly linked to the DNA gene sequences to be expressed, or introduced into the same cell by co-transfection.

Additional elements of the vectors may also be useful for obtaining an optimal production of proteins of the invention, in particular for selecting a particular cell containing plasmid or viral vector: the ease with which recipient cells, that contain the vector may be recognized and selected from those recipient cells which do not contain the vector; the number of copies of the vector which are desired in a particular host; and whether it is desirable to be able to "shuttle" the vector between host cells of different species.

Once the vector(s) or DNA sequence containing the construct(s) has been prepared for expression the DNA construct(s) may be introduced into an appropriate host cell by any of a variety of suitable means: transformation, transfection, conjugation, protoplast fusion, electroporation, calcium phosphate-precipitation, direct microinjection, etc.

Host cells may be either prokaryotic or eukaryotic. Preferred are eukaryotic hosts, e.g. mammalian cells, such as human, monkey, mouse, and Chinese Hamster Ovary (CHO) cells, because they provide post-translational modifications to protein molecules, including correct folding or glycosylation at correct sites. Also yeast cells can carry out post-translational peptide modifications including glycosylation. A number of recombinant DNA strategies exist which utilize strong promoter sequences and high copy number of plasmids that can be utilized for production of the desired proteins in yeast. Yeast recognizes leader sequences on cloned mammalian gene products and secretes peptides bearing leader sequences (i.e., pre-peptides).

After the introduction of the vector(s), the host cells are grown in a selective medium, which selects for the growth of vector-containing cells. Expression of the cloned gene sequence(s) results in the production of the desired proteins.

These objects of the invention can be achieved by combining the disclosure provided by the present patent application on antagonists of MCP proteins, with the knowledge of common molecular biology techniques. Many reviews (Makrides S C, 1999) and books provides teachings on how to clone and produce recombinant proteins using vectors and Prokaryotic or Eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001).

Examples of chemical synthesis technologies are solid phase synthesis and liquid phase synthesis. As a solid phase synthesis, for example, the amino acid corresponding to the C-terminus of the peptide to be synthetized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoc (t-butoxycarbonyl), Cl-Z (2-chlorobenzyloxycarbonyl), Br-Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Cl2-Bzl (2,6-dichlorobenzyl) for the amino groups; $NO_2$ (nitro) and Pmc (2,2,5,7,8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method. Totally synthetic MCP proteins are disclosed in the literature (Brown A et al., 1996).

Purification of the natural, synthetic or recombinant MCP antagonists of the invention can be carried out by any one of the methods known for this purpose, i.e. any conventional procedure involving extraction, precipitation, chromatography, electrophoresis, or the like. A further purification procedure that may be used in preference for purifying the protein of the invention is affinity chromatography using monoclonal antibodies or affinity groups, which bind the target protein and are produced and immobilized on a gel matrix contained within a column. Impure preparations containing the proteins are passed through the column. The protein will be bound to the column by heparin or by the specific antibody while the impurities will pass through. After washing, the protein is eluted from the gel by a change in pH or ionic strength. Alternatively, HPLC (High Performance Liquid Chromatography) can be used. The elution can be carried using a water-acetonitrile-based solvent commonly employed for protein purification. The invention includes purified preparations of the compounds of the invention. Purified preparations, as used herein, refers to the preparations which are at least 1%, preferably at least 5%, by dry weight of the compounds of the invention.

Another object of the present invention is the use of MCP antagonists as above defined as medicaments, in particular as the active ingredients in pharmaceutical compositions (and formulated in combination with pharmaceutically acceptable carriers, excipients, stabilizers, or diluents) for treating or preventing diseases related to an undesirable activity of MCP proteins leading to an excessive migration and activation of leukocytes expressing their receptors, such as autoimmune and inflammatory diseases as well as bacterial and viral infections. Non-limitative examples of such diseases are the following: arthritis, rheumatoid arthritis (RA), psoriatic arthritis, psioriasis, osteoarthritis, systemic lupus erythematosus (SLE), systemic sclerosis, scleroderma, polymyositis, glomerulonephritis, fibrosis, lung fibrosis, allergic or hypersensitvity diseases, dermatitis, Type IV hypersensitivity also called delayed-type hypersensitivity or DTH, asthma, chronic obstructive pulmonary disease (COPD), inflammatory bowel disease (IBD), Crohn's disease, ulcerative colitis, multiple sclerosis, septic shock, HIV-infection, transplantation, graft-versus-host disease (GVHD), endometriosis, pancreatitis, thyroiditis, encephalopathies.

In view of the literature on the subject, MCP proteins antagonists can be as active ingredients in pharmaceutical compositions for the treatment or prevention of other diseases related to an undesirable activity of MCP proteins, such as vascular disorders (restenosis after coronary intervention, arteriosclerosis, atherosclerosis, ischemia, stroke) or cancer.

Another object of the present invention is, therefore, the method for treating or preventing any of the above mentioned diseases comprising the administration of an effective amount of an MCP protein antagonist of the invention.

The pharmaceutical compositions may contain, in addition to the MCP antagonist, suitable pharmaceutically acceptable carriers, biologically compatible vehicles and additives which are suitable for administration to an animal (for example, physiological saline) and eventually comprising auxiliaries (like excipients, stabilizers or diluents) which facilitate the processing of the active compounds into preparations which can be used pharmaceutically. Such compositions can be eventually combined with another therapeutic composition acting synergically or in a coordinated manner with the MCP mutants of the invention. For example, similar synergistic properties of CC-chemokine antagonists have been demonstrated in combination with cyclosporin (WO 00/16796). Alternatively, the other composition can be based with a compound known to be therapeutically active against the specific disease (for example, IFN-beta for multiple sclerosis, soluble TNF receptors for rheumatoid arthritis).

The pharmaceutical compositions may be formulated in any acceptable way to meet the needs of the mode of administration. For example, the use of biomaterials and other polymers for drug delivery, as well the different techniques and models to validate a specific mode of administration, are disclosed in literature (Luo B and Prestwich G D, 2001; Cleland J L et al., 2001).

An "effective amount" refers to an amount of the active ingredients that is sufficient to affect the course and the severity of the disease, leading to the reduction or remission of such pathology. The effective amount will depend on the route of administration and the condition of the patient.

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution.

Any accepted mode of administration can be used and determined by those skilled in the art to establish the desired blood levels of the active ingredients. For example, administration may be by various parenteral routes such as subcutaneous, intravenous, intradermal, intramuscular, intraperitoneal, intranasal, transdermal, rectal, oral, or buccal routes. Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99 percent, preferably from about 20 to 75 percent of active compound together with the excipient. Compositions which can be administered rectally include suppositories.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredient is comprised between 0.01 to 100 milligrams per kilogram of body weight. Ordinarily 1 to 40 milligrams per kilogram per day given in divided doses or in sustained release form is effective to obtain the desired results. Second or subsequent administrations can be performed at a dosage, which is the same, less than, or greater than the initial or previous dose administered to the individual.

The present invention has been described with reference to the specific embodiments, but the content of the description comprises all modifications and substitutions, which can be brought by a person skilled in the art without extending beyond the meaning and purpose of the claims.

The invention will now be described by means of the following Examples, which should not be construed as in any way limiting the present invention. The Examples will refer to the Figures specified here below.

EXAMPLES

Example 1

In Vitro Characterization of the Non-heparin Binding MCP-1 Mutant MCP-1WT*2A

Materials and Methods

Expression of the MCP-1 Mutants MCP-1WT* and MCP-1WT*2A.

MCP-1 mutants were generated by in vitro, PCR-based mutagenesis of the DNA sequence coding for human MCP-1 (hMCP-1; FIG. 1; SEQ ID NO: 1), and in particular for the mature form of human MCP-1, corresponding to the segment 24-99 of the precursor molecule (SWISSPROT Acc. No P13500).

It was first generated a plasmid encoding for an active mutant MCP-1 protein called MCP-1WT*, in which a Methionine start codon is added at the N-terminal of sequence coding for human MCP-1 (24-99) and an internal Methionine (amino acid 87 in the precursor and 64 in the mature protein) is replaced with an Isoleucine. This substitution avoids, when the plasmid is used for the expression in E. coli, the formation of undesirable MCP-1 species containing Methionine Sulfoxide, without affecting the properties typical of MCP-1 (Paavola C D et al, 1998). The resulting sequence, called MCP-1WT*, was cloned and expressed in E. coli by making use of a plasmid based on the pET3 plasmid (Paavola C D et al, 1998) as a protein containing 77 residues (FIG. 1A; SEQ ID NO: 2).

The plasmid expressing MCP-1WT* was then further mutagenized by cloning a PCR fragment encoding for two Alanines instead of Arginine and Lysine in positions 41 and 42 of human MCP-1 precursor (position 18 and 19 in the mature protein), in order to generate the MCP-1 mutant MCP-1WT*2A, having the same length and purification features of MCP-1WT* (FIG. 1; SEQ ID NO: 3).

All constructs were obtained and controlled by standard molecular biology technologies (PCR mutagenesis and amplification, DNA sequencing, restriction digestion) and maintained in the DH5alpha strain of E. coli during the cloning process. The coding sequences were chosen in order to have an optimal codon usage for the expression in E. coli i (Kane J F, 1995).

The pET3-based plasmids encoding for MCP-1WT* and MCP-1WT*2A were then transferred in an E. coli BL21 (pLys)-derived strain called TAP302 and the resulting strains were used the recombinant expression of the MCP-1 mutants as described (Paavola C D et al, 1998). This protocol includes the use of aminopeptidase to remove the N-terminal methionine, thus obtaining recombinant MCP-1 mutants having the same length of the natural mature form (76 amino acids; FIG. 1B). The identity of the recombinant proteins was verified by mass spectrometry.

Chromatographic assays of MCP-1WT* and MCP-1WT*2A.

MCP-1WT* and MCP-1WT*2A were loaded either onto a Heparin Sepharose column or onto a SP Sepharose cation exchange column. In both cases the column was equilibrated in 10 mM potassium phosphate (pH 7.5) and the protein was eluted with a linear gradient from 0 to 1 M NaCl in the same buffer.

Heparin Binding Assay of MCP-1WT* and MCP-1WT*2A.

Serial dilutions of MCP-1WT* mutants in Phosphate Buffer Saline (PBS) covering the range of 0.02-30 μM were incubated with 170 nM of [$^3$H]-heparin for 1 hour at 37° C. Triplicates of 20 μl of each sample were transferred to a 96 well P81 Unifilter plate (Whatman Inc) fitted with a nitrocullose filter. The plate was washed three times with 200 μl of PBS using a vacuum pump to remove unbound labelled heparin. Scintillation fluid (50 μl) was added to each well and radioactivity counted (1 minute/well) in a beta counter. Data were analysed using Prism program (GraphPad Software).

Equilibrium Competition Receptor Binding Assays

The assays were carried out on membranes from Chinese Hamster Ovary (CHO) cells stably expressing the MCP-1 receptor (CCR2), using a Scintillation Proximity Assay (SPA) and [$^{125}$I]-MCP-1 as tracer. The radiolabelled chemokine (specific activity of 2200 mCi/mole) was generated from recombinant mature MCP-1 according to the [$^{125}$I] supplier (Amersham). Competitors were prepared by serial dilutions (range $10^{-6}$-$10^{-12}$ M) of the unlabelled MCP-1 mutant in the binding buffer (50 mM HEPES pH 7.2, 1 mM $CaCl_2$, 5 mM $MgCl_2$, 0.15 M NaCl and 0.5% BSA).

Wheat germ SPA beads (Amersham) were suspended in PBS to 50 mg/ml, and diluted in the binding buffer to a 10 mg/ml, and the final concentration in the assay was 0.25 mg/well. Membranes expressing CCR2 were stored at −80° C. and diluted in the binding buffer to 80 μg/ml. The final membrane concentration was 2 μg/well and that of [$^{125}$I]-MCP-1 was 0.1 nM. The plates were incubated at room temperature with agitation for 4 hours. Radioactivity was counted (1 minute/well) in a beta counter. Data from triplicate samples were analysed using Grafit program (Erithacus Software).

Results

The literature shows different approaches for testing the heparin/GAG binding properties of MCP-1 (Hoogewerf A J et al., 1997; Kuschert G et al., 1999; Ali S et al., 2001; Patel D et al., 2001; Chakravarty L et al, 1998).

Two mutants of MCP-1, whose sequence is based on the mature form of human MCP-1 (FIG. 1), were expressed in E. coli. The first one, MCP-1WT*, corresponds to mature human MCP-1 precursor with a mutation known to eliminate the possibility of methionine oxidation, without interfering with the binding properties and activity typical of MCP-1 (Paavola C D et al, 1998). On the basis of the sequence of this "active" mutant, a second mutant, MCP-1WT*2A was expressed in which a dibasic site at the N-terminal was additionally replaced with Alanine residues.

The effect of this latter substitution on the MCP-1 properties was first tested by heparin chromatography. The elution profiles of the two mutants applied on this chromatography column differ considerably, since the concentration of NaCl required to elute MCP-1WT* was 0.54 M NaCl whilst MCP-1WT*2A was eluted at 0.24 M NaCl. A smaller difference was measured using cation exchange chromatography on a SP Sepharose column (0.55 M NaCl against 0.27 M NaCl).

The comparison of the elution profiles on such chromatographic media provides a qualitative indication on the contribution of non-specific electrostatic interactions due to basic amino acids to the heparin binding properties (Proudfoot A et al., 2001). The difference in NaCl concentration obtained on cation exchange chromatography is subtracted from that obtained on heparin chromatography. According to this method, when the resulting figure is positive (0.02 M, in this case), it can be concluded that a specific interaction with heparin is identified as being associated to the dibasic site mutated in MCP-1WT*2A.

A direct measure of binding to heparin was then performed using tritiated heparin and serial dilution of the *E. coli* expressed MCP-1 mutants (FIG. 2). Protein-Heparin complexes were isolated by adding the dilutions onto nitrocellulose filters. Such supports are capable of retaining proteins efficiently, therefore allowing the evaluation of amount of the radiolabelled heparin bound to the protein. This approach confirmed that the heparin binding properties of MCP-1WT*2A were significantly reduced compared to MCP-1WT*.

Figure 3:
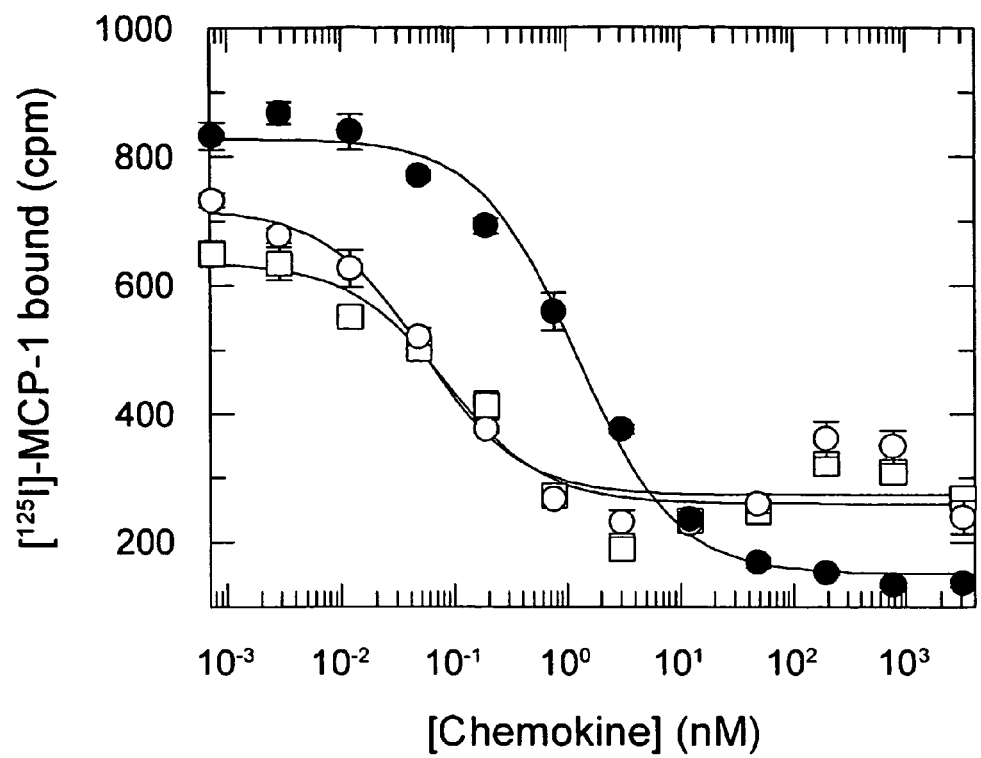
FIG. 3: graph representing the results of the equilibrium competition receptor binding assay performed by monitoring the displacement of [$^{125}$I]-MCP-1 from CCR2-expressing CHO membranes consequent to the addition, as chemokine, of hMCP-1 (□), MCP-1WT* (○), or MCP-1WT*2A (●).

Finally, an equilibrium competition receptor binding assay was performed to demonstrate the effect of the reduced heparin binding properties of MCP-1WT*2A on the binding of the specific receptor CCR2 (FIG. 3). Samples containing radiolabelled MCP-1 mixed with serial dilutions of one of the two mutants, or of MCP-1, were incubated with membranes prepared from CHO cells stably expressing CCR2. Whilst MCP-1WT* and MCP-1 protein showed an almost identical binding profile, the MCP-1WT*2A mutant shows a 20 fold reduction in affinity for CCR2, since it has an $IC_{50}$ of 1.73±0.6 nM, compared to 0.08±0.045 nM for the other two tested proteins, showing that high affinity is retained in this heparin-binding defective MCP-1 mutant.

Example 2

Characterization of the Non-heparin Binding MCP-1 Mutant in Models of Cell Recruitment Materials and Methods
Chemotaxis Assay The assay was carried out using a human pro-monocytic cell line (THP-1) in 24-well transwell chemotaxis chambers (Costar) fitted with 5 μm pore size membranes (Neuroprobe). The recombinant MCP-1 proteins were serially diluted (range of $10^{-6}$-$10^{-12}$ M) in 600 μl of RPMI medium containing 5% inactivated fetal calf serum (FCS), 2 mM glutamine and 25 mM HEPES (pH 7.2). These samples were placed in the lower wells, whilst THP-1 cells (100 μl of a cell suspension at $10 \times 10^6$ cells/ml in the same medium) were placed in the inserts. The chamber was incubated for 3 hours at 37° C. under 5% $CO_2$. The samples were then removed, transferred to a 1.5 ml tube, and centrifuged at 200×g for 5 minutes. The pelleted cells were resuspended in 100 ml PBS and counted in a Coulter counter (Beckman). The data were analyzed using Prism program (GraphPad Software).

Peritoneal Cellular Recruitment Assay

Cellular recruitment was induced by intraperitoneal injection of female BALB/c mice of 8 to 12 wk of age of 10 μg of the recombinant MCP-1WT* or MCP-1WT*2A proteins diluted in 0.2-ml sterile, lipopolysaccharide-free PBS. When the antagonistic properties of MCP-1WT*2A were tested, the indicated amounts of the protein, diluted in 0.2 ml of the same sterile solution, were administered 30 minutes prior to the agonist (MCP-1WT*) administration. Mice were sacrificed by aerosolized $CO_2$ 16 hours after the administration of the agonist, and peritoneal lavage was performed with 5 ml PBS three times. The lavages were pooled and centrifuged at 600×g for 10 minutes, and the pelleted cells were resuspended in a final volume of 1 ml and total elicited leukocytes were counted with a hemacytometer.

Results

Cell recruitment assays have been used for characterizing properties of different proteins related to MCP-1 (Ajuebor M N et al., 1998; Reckless J and Grainger D J, 1999; Kaji M et al., 2001)

Figure 4:
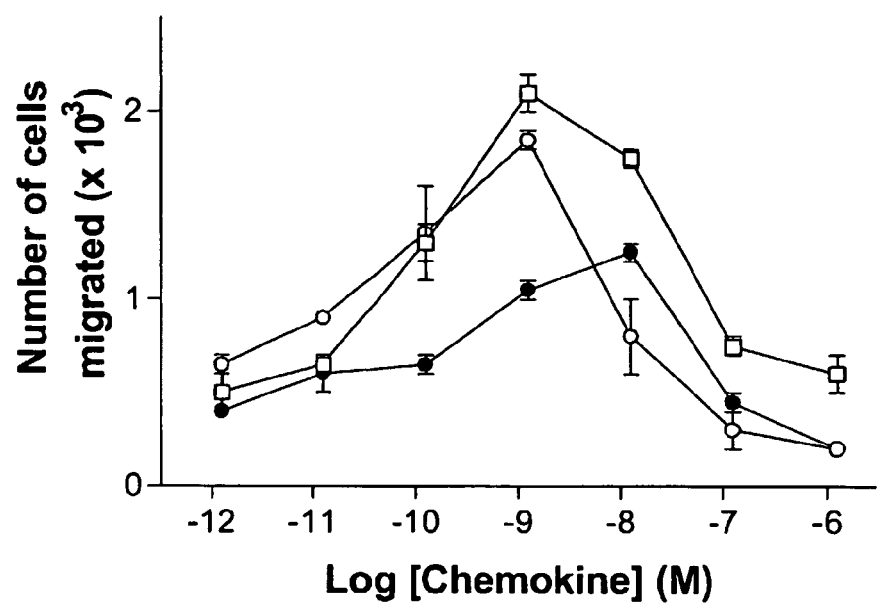
FIG. 4: graph representing the results of the transwell chemotaxis assay performed using THP-1 cells and, as chemotactic agent, recombinant human MCP-1 (□), MCP-1WT*, (○) or MCP-1WT*2A (●).

The results obtained for MCP-1WT*2A in a chemotaxis assay on human monocytes (THP-1 cell line) correspond well with those obtained in the receptor-binding assay described in Example 1. MCP-1WT*2A was able to induce a robust response (6-fold over baseline) of THP-1 chemotaxis although maximum activity was observed at 10 nM compared to 1 nM for the wild type proteins, which induced a 9-fold increase over baseline (FIG. 4).

Figure 5:
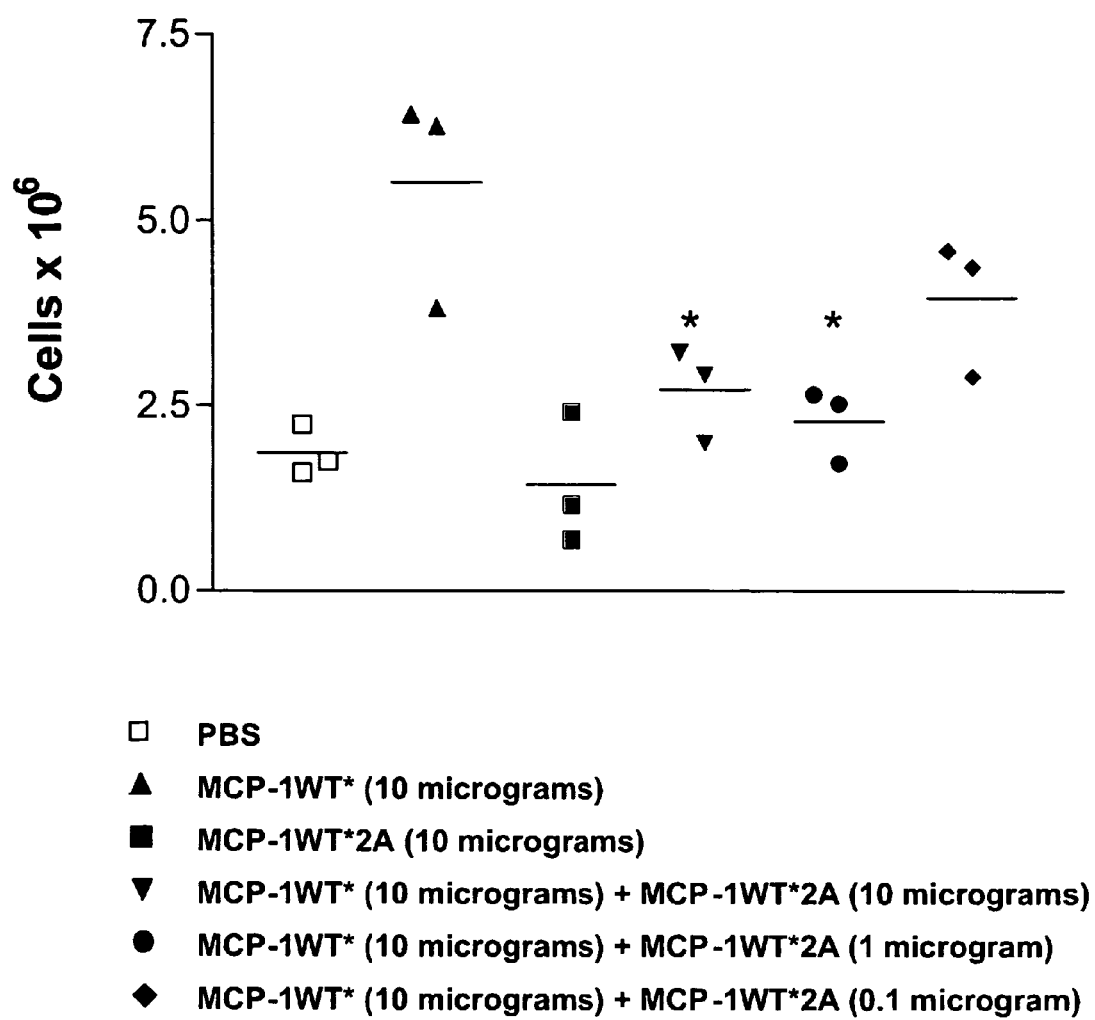
FIG. 5: graph summarizing the results of the peritoneal cells recruitment assay, performed in mice using MCP-1WT* and/or MCP-1WT*2A. The concentrations of MCP-1WT*2A showing a statistically significant inhibition activity on the number of cells recruited by MCP-1WT* are indicated in the graph with *.

The activity of MCP-1WT*2A as an antagonist or agonist of MCP-1 was also evaluated using a peritoneal cellular recruitment assay (FIG. 5). When MCP-1WT* and MCP-1WT*2A are administered, the heparin-binding defective mutant was unable to induce cellular recruitment into the peritoneum at the dose (10 micrograms/mouse) that MCP-1WT* causes substantial recruitment. Furthermore, if MCP-1WT*2A is administered 30 minutes prior to the administration of MCP-1WT*, the cellular recruitment induced by MCP-1WT* is significantly antagonized in a dose dependent manner. Therefore, the abrogation of GAG-binding in MCP-1 produces an antagonist of MCP-1 capable of inhibiting in vivo the cellular recruitment induced by MCP-1.

Example 3

Characterization of a Non-heparin Binding MCP-1 Mutant in Animal-based Models

Materials and Methods
Delayed Contact Hypersensitivity Model

The mouse ear-swelling test to measure contact hypersensitivity was performed as previously described (Garrigue J L et al., 1994). Briefly, mice were pre-sensitized topically by applying 25 μl of 0.5% 2,4-dinitrofluorobenzene (DNFB; Sigma Chemical Co.) solution in acetone/olive oil (4:1) to the shaved abdomen. Five days later, 20 μl of 0.2% DNFB in the same vehicle was applied to the right ears, and vehicle alone to the left ears. Mice were treated daily from Day 5 to 9 with an intraperitoneal administration of either 0.5 mg/kg (10 micrograms/mouse) of MCP-1WT* or PBS only in the control group. The first treatment was administered 1 hour prior to the DNFB challenge. Ear thickness was measured with a dial thickness gauge (Mitutoyo Corp.), and ear swelling was estimated by subtracting the pre-challenge from the post-challenge value, and by further subtracting any swelling detected in the vehicle-challenged contralateral ear.

Bleomycin Induced Lung Fibrosis Model

C57BU6 female mice received bleomycin (3.75 U/kg in 25 µl PBS) intra-tracheally (day 0). One hour after the instillation of bleomycin, test animals received intraperitoneally either 0.25 mg/kg MCP-1WT*2A in 0.2 ml PBS or only 0.2 ml PBS. This treatment was given daily and continued for 10 days. The body weight loss and percentage of mortality were recorded daily. At day 10, all mice were sacrified by $CO_2$ asphyxiation. Four lung lobes were placed at −80° C. for measurement of hydroxyproline levels as an indication of collagen deposition as well as one lobe processed for histological determination of pulmonary fibrosis. Total lung collagen was determined by the analysis of hydroxyproline. Briefly, lungs were homogenized in Tris-HCl (pH 7.6) with a Tissue Tearor followed by incubation in Amberlite overnight at 115° C. Citrate/acetate buffer, isopropanol, chloramine-T and DAB solutions were added to the samples and left for 30 minutes at 60° C. Samples were cooled at room temperature for 10 minutes and read at 560 nm on spectrophotometer. Pulmonary fibrosis was also determined histologically by fixation of the right lung lobe in 10% Formalin, followed by embedding in paraffin, sectioning, and staining with Masson's trichrome solution. Histological changes were examined by light microscopy. Morphological evaluation of bleomycin-induced lung inflammation and fibrosis was performed using a semi-quantitative scoring method, calculating the percentage of the fibrotic area.

Experimental Autoimmune Encephalomyelitis (EAE) Model

Female mice (8-week old; C57 BU6NCrIBR strain; 18-22 grams of weight) were immunized at day 0 by injecting 0.2 ml of an emulsion containing the $MOG_{35-55}$ peptide (200 micrograms) and *Mycobacterium tuberculosis* (500 micrograms) in Complete Freund's Adjuvant (CFA; Difco Lab.) subcutaneously in the left flank. Immediately afterwards, pertussis toxin (500 nanograms in 400 microliters of a buffer containing 0.5 M NaCl, 15 mM Tris (pH 7.5), 0.017% Triton X-100) was administered intraperitoneally. On day 2 the animals were given a second intraperitoneal injection of the same solution containing pertussis toxin. On day 7, the mice were administered a second dose of $MOG_{35-55}$ peptide (200 micrograms) in CFA injected subcutaneously in the right flank. This procedure results in disease onset at approximately day 18-20, with the appearance of a progressive paralysis, arising from the tail and progressively ascending up to the forelimbs.

The treatment was started for each animal at experimental day 7 (approximately 1-3 days before the usual occurrence of the disease) and continued for 21 consecutive days. Starting from day 7, the animals were examined individually for the presence of paralysis by means of a clinical score as follows:

0=no sign of disease
0.5=partial tail paralysis
1=tail paralysis
1.5=tail paralysis+partial unilateral hindlimb paralysis
2=tail paralysis+hindlimb weakness or partial hindlimb paralysis
2.5=tail paralysis+partial hindlimb paralysis (lowered pelvis)
3=tail paralysis+complete hindlimb paralysis
3.5=tail paralysis+complete hindlimb paralysis+incontinence
4=tail paralysis+hindlimb paralysis+weakness or partial paralysis of forelimbs
5=moribund or dead The experiment was carried out with three groups of 10 animals each, as indicated below. Group 1 was treated with PBS as the positive control. Group 2 was treated daily with an intraperitoneal injection of 0.05 mg/kg of MCP-1WT*2A. Group 3 was treated daily with an intraperitoneal injection of 0.5 mg/kg of MCP-1WT*2A. The MCP-1WT*2A mutant protein was dissolved in sterile water and then diluted into sterile PBS (200 microliters/mouse) to attain the required concentration.

Collagen Induced Arthritis (CIA) Model

Male mice (8-12 week old; DBA/1 strain; 18-22 grams of weight) were immunized at day 0 by intradermal injection at the base of the tail with 0.2 ml of an emulsion composed of bovine type II collagen (100 micrograms; Morwell Diagnostics) and *Mycobacterium tuberculosis* (400 micrograms) in Complete Freund's Adjuvant (CFA; Difco Lab.).

Starting approximately from day 16-20, the signs of inflammation appeared, affecting one or more limbs. The animals were graded individually for disease severity by means of a clinical score, based on visual clinical score for the presence of inflammation in the fingers of the forepaws and hind paws, and composed as follows:

0=no sign of disease
0.5=from 1 to 5 fingers/toes with signs of inflammation
1=from 6 to 10 fingers/toes with signs of inflammation
1.5=from 11 to 15 fingers/toes with signs of inflammation
2=from 16 to 20 fingers/toes with signs of inflammation Two groups (n=10 mice) having a total clinical score >0.5 were daily treated for 7 consecutive days with intraperitoneal injections of PBS (control group) or with 0.05 mg/kg of MCP-1WT*2A. All the animals were sacrificed 24 hours after the last treatment.

Ovalbumin Induced Lung Inflammation (OVA) Model

Female mice (8-10 weeks old; Balb/c strain). Mice were sensitized by an intraperitoneal injection of 10 µg ovalbumin (Sigma) precipitated in 2 mg aluminium hydroxide 2% (Serva) in a total volume of 200 µl. The aluminium hydroxide 2%/ovalbumin solution was prepared by mixing 25 µl ovalbumin (2 mg/ml), 250 µl aluminium hydroxide in 725 µl LPS-free 0.9% NaCl and precipitated 3-4 hours at 4° C. Fifteen days after sensitization, mice were treated and challenged in groups of 6 mice as follows:

Group 1: challenged with LPS-free 0.9% NaCl and treated with PBS (baseline)
Group 2: challenged with ovalbumin and treated with PBS (negative control)
Group 3: challenged with ovalbumin and treated with 0.5 mg/kg MCP-1WT*2A PBS or MCP-1WT*2A were administered by intraperitoneal injection (200 microliters) 30 minutes before each challenge on five consecutive days. Mice were challenged intranasally, with ovalbumin (15 micrograms of precipitated ovalbumin resusped in 50 microliters LPS-free 0.9% NaCl) under inhaled anaesthesia with Isoflurane. At 72 hours post-challenge, mice were killed by a lethal intraperitoneal injection of 300 µl 14% Urethane (v:v) in 0.9% NaCl. The trachea was trimmed free of connective tissue, and a small incision was made to insert a catheter of 0.75 millimeters diameter into the trachea. The cannula was tied in place with a piece of suture thread and was attached to 1-ml syringe. Lungs were filled in situ with 0.4 millililter PBS. Fluid was withdrawn from the lungs after gentle massage to remove cells and collected in a plastic tube on ice. This procedure was repeated 4 times and the cell suspensions recovered from each animal were combined on ice to give a final volume of approximately 1.4 ml. Cell counting was performed using a hemacytometer using a 2-fold dilution of the cell suspension into Trypan blue.

Results

The in vivo properties of MCP-1 have been characterized in many articles, in particular by making use of transgenic mice (Lu B et al., 1998; Rutledge B J et al., 1995). MCP-1WT*2A were then tested by making use of animal models for human inflammation and diseases to confirm the results on the antagonistic activity of this MCP-1 heparin-binding defective mutant obtained using the peritoneal cell recruitment model.

Figure 6:
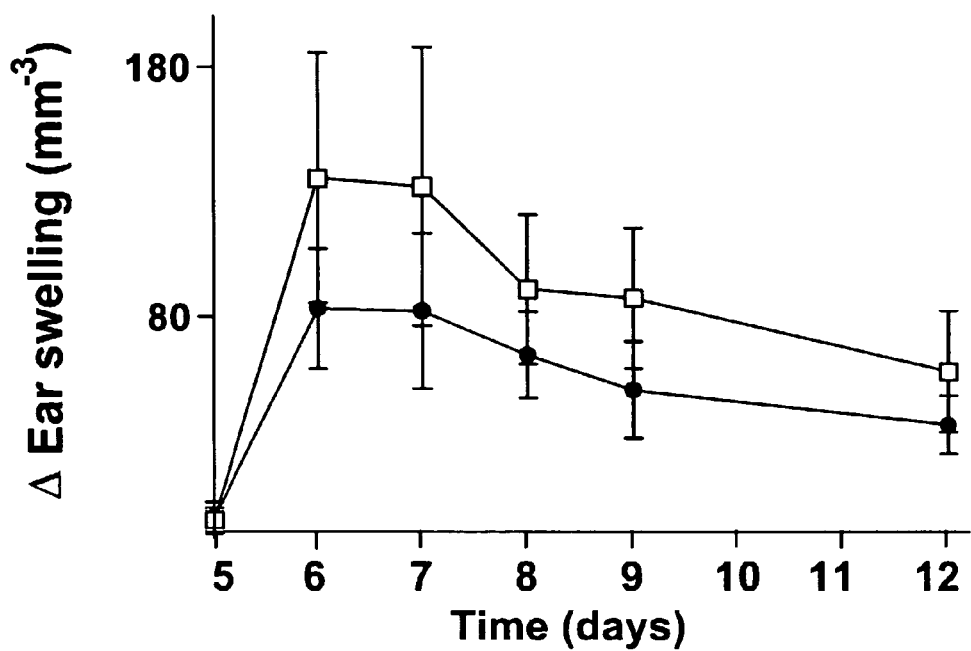
FIG. 6: graph summarizing the results of the delayed contact hypersensitivity assay. Mice were treated with 0.5 mg/kg MCP-1WT*2A (■) or with vehicle only (□). The effect is measured in terms of ear swelling volume each day during treatment.

Delayed contact hypersensitivity is an animal model in which a hapten-specific skin inflammation mediated by T cells is measured by ear swelling. Enhanced contact hypersensitivity has been shown in transgenic mice that constitutively produce high levels of MCP-1 in the sera (Mizumoto N et al., 2001). The ear skin of normal mice was challenged by making use of the contact sensitizer 2,4-dinitrofluorobenzene (DNFB) as hapten. The consequent swelling was significantly lower in mice treated with an intraperitoneal administration of MCP-1WT*2A (starting at the time of challenge with DNFB), when compared to the effect observed in mice treated with vehicle alone, throughout the treatment period (FIG. 6).

The properties of MCP-1WT*2A were tested in a lung inflammation/fibrosis model, since it is known that MCP-1 induces procollagen deposition in pulmonary or skin inflammatory processes (Hogaboam C M et al., 1999).

Figure 7:
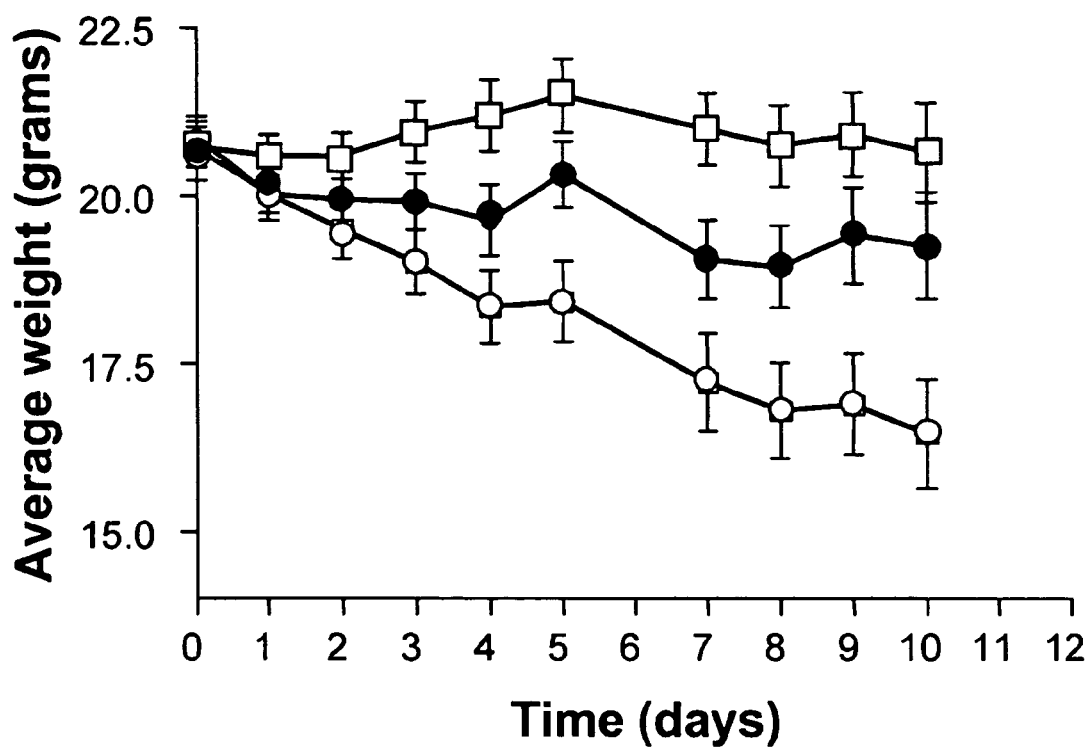
FIG. 7: graph summarizing the effects on body weight of mice receiving bleomycin for inducing lung fibrosis. The average weight of control mice (□) is compared with the average weight of treated mice receiving as well an intraperitoneal administration of 0.25 mg/kg MCP-1WT*2A (●) or PBS only (○). The indicated weight is an average weight value for each group of mice.

Intratracheal instillation of bleomycin in mice results in lung inflammation and fibrosis within 7 to 10 days respectively, with a marked accumulation of collagen in the lungs as well as a rapid decrease of weight (Chen E S et al., 2001). Weight was recorded throughout the 10 days after the exposure to bleomycin in mice treated 1 hour later with an intraperitoneal administration of MCP-1WT*2A or only with PBS, and further compared to a control group not treated with bleomycin. As it is clearly evident starting from day 2, PBS-treated control mice lose a significantly higher amount of weight compared to MCP-1WT*2A treated mice (FIG. 7). Lung fibrosis and inflammation was evaluated after sacrificing the animals at day 10 using two different methods. It is known that bleomycin increases lung hydroxyproline synthesis proportionally to collagen synthesis and fibrosis (Madtes D K et al., 1999). The hydroxyproline level s measured in mice treated with PBS only were significantly higher than the levels measured in the group receiving an intraperitoneal administration of MCP-1WT*2A. Indeed, the levels in this latter group were comparable to non-bleomycin treated mice. Another semi quantitative histological assessment confirmed the significant reduction in total levels of fibrosis in the MCP-1WT*2A treated group versus control (FIG. 8).

Figure 9:
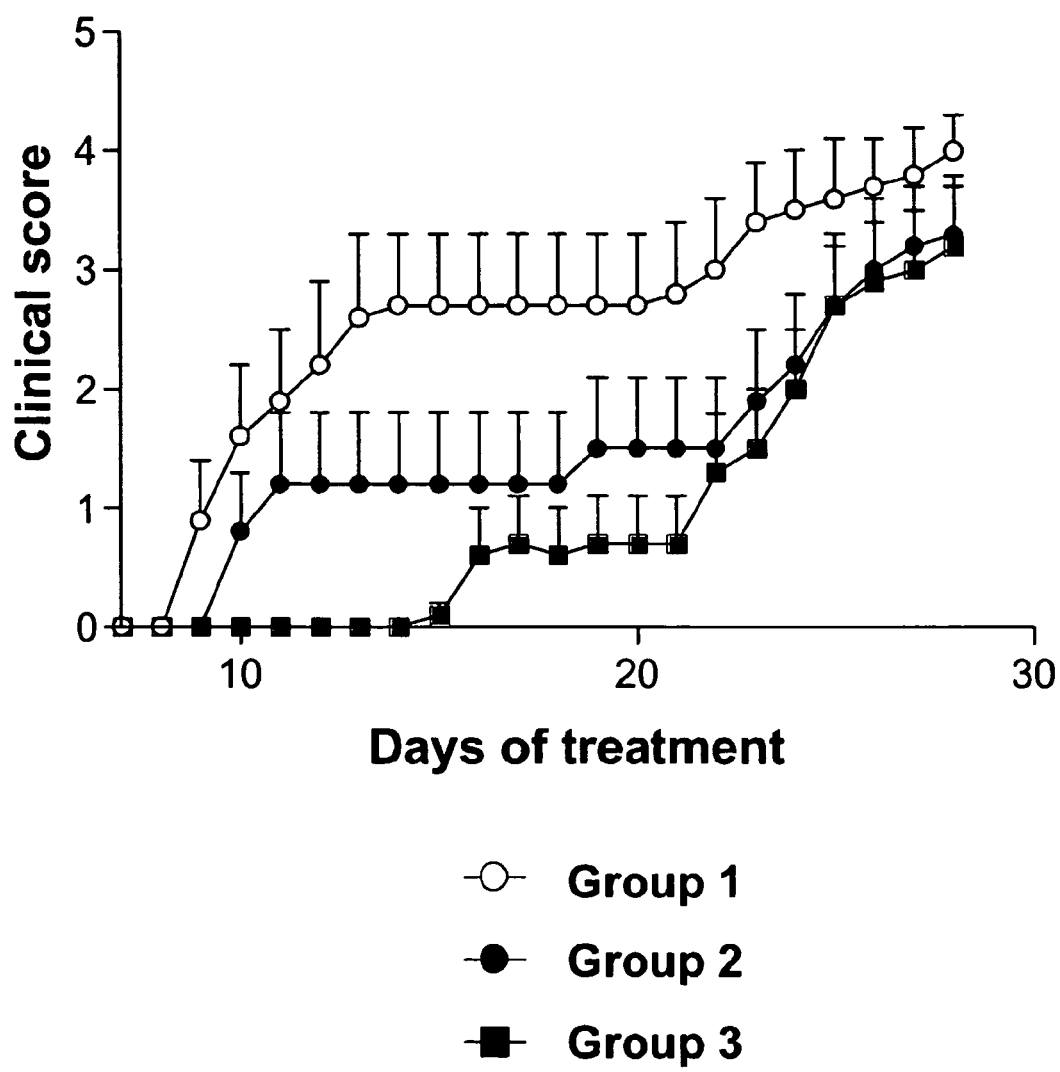
FIG. 9: graph comparing the clinical score measured in Experimental Autoimmune Encephalomyelitis (EAE) animal models treated with PBS only (Group 1), 1 microgram/mouse of MCP-1WT*2A (Group 2), or 10 micrograms/mouse of MCP-1WT*2A (Group 3).

Antibodies against MCP-1 and transgenic mice lacking a functional MCP-1 gene demonstrated the crucial role of MCP-1 for macrophage recruitment and inflammation in central nervous system associated, for example, to Herpesvirus-Induced Encephalomyelitis (HSM) and Experimental Autoimmune Encephalomyelitis (EAE), the animal model for multiple sclerosis (Nakajima H et al., 2001; Huang D R et al., 2001). The administration of MCP-1WT*2A considerably improved the clinical score of EAE animal model at both the tested doses (FIG. 9).

Figure 10:
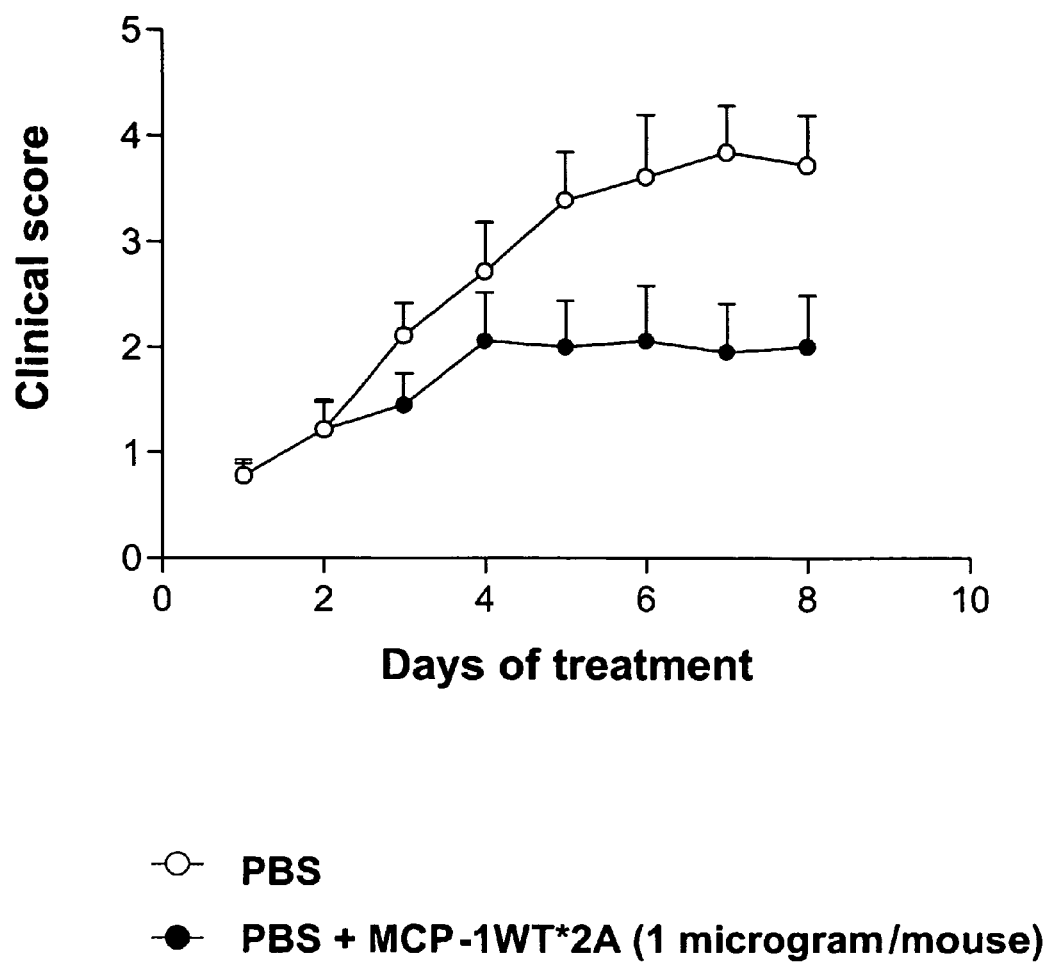
FIG. 10: graph comparing the clinical score measured in collagen induced arthritis (CIA) animal models treated with PBS only, or 1 microgram/mouse of MCP-1WT*2A.

As discussed above, MCP-1 has a strong fibrogenic effect. The properties of MCP-1WT*2A against this MCP-1 activity were tested in the Collagen-induced Arthritis (CIA) model. Also in this case, MCP-1WT*2A considerably improved the clinical score of the treated mice (FIG. 10).

Figure 11:
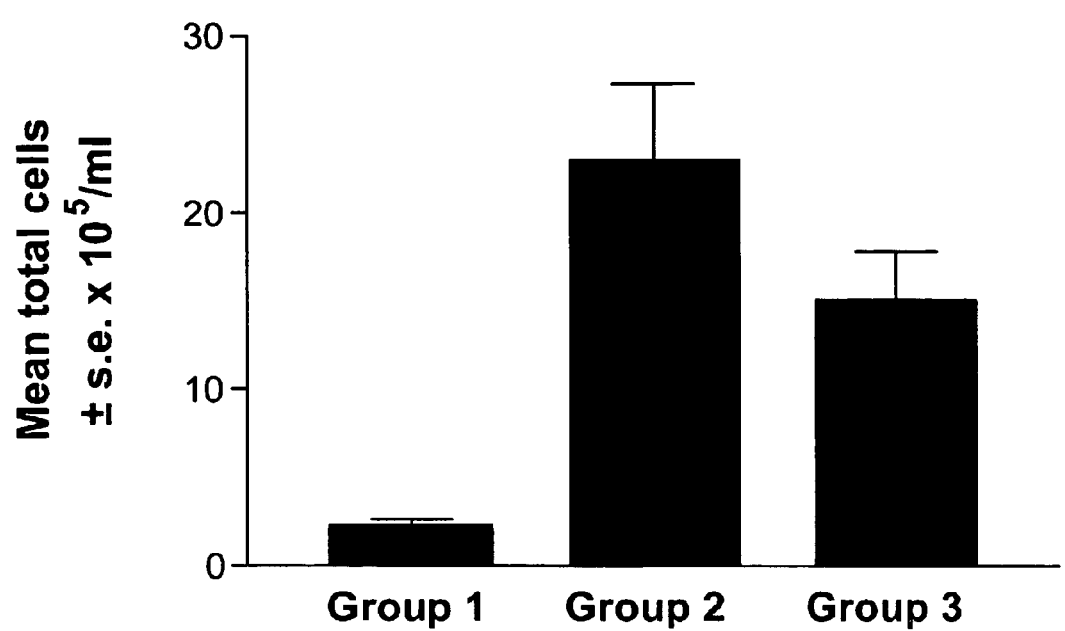
FIG. 11: graph comparing the amount of cells isolated from trachea of animal models treated and challenged with PBS only (Group 1), treated with PBS and challenged with ovalbumin (Group 2), or treated with 10 microgram/mouse of MCP-1WT*2A and challenged with ovalbumin (Group 3).

Lung allergic inflammation and bronchial hyperresponsiveness (BHR) that characterize asthma is achieved by the accumulation and activation of different leukocyte subsets in the lung. Blockage of MCP-1 by means of antibodies diminishes drastically BHR and inflammation (Gonzalo J A et al., 1998). In the ovalbumin-induced lung inflammation (OVA) model, MCP-1WT*2A provided significant improvement, in terms of reduced cell recruitment (FIG. 11).

Given that the dibasic site mutated in the examples of the present invention, together with the other residues known to be involved in MCP-1 binding to GAG such as Histidine 66 and Lysine 58 (Chakravarty L et al., 1999), is conserved in all MCPs (FIG. 1B), other MCPs-based mutants having antagonistic activities can be designed on the basis of the findings of this patent application.

In particular, MCP antagonists can be double mutants of human mature MCP-1 (SEQ ID NO: 4), MCP-2 (SEQ ID NO: 5), MCP-3 (SEQ ID NO: 6), MCP-4 (SEQ ID NO: 7), or Eotaxin (SEQ ID NO: 8) in the positions 18 and 19, 18 and 58 (or 66), 19 and 58 (or 66), as well as triple mutants in the positions 18, 19 and 58 (or 66; the numbering corresponds the one given for human mature MCP-1). Other residues that can be mutated additionally to the ones in positions 18 and 19 are the other basic residues identified as highly conserved in all human MCP proteins (residues 24, 44, 49, 75; FIG. 1B).

The properties of these alternative molecules can be tested by any of the methods above described, as well as by making use of other validating approaches known in the art. Many other useful chemokine-related technologies (recombinant expression, in vitro assays, transgenic animals) are extensively reviewed in literature ("Chemokine Protocols", Methods in Molecular Biology vol. 138, Humana Press, 2000; "Chemokine Receptors", Methods in Enzymology vol. 288. Academic Press, 1997).

TABLE I

| Amino Acid | Synonymous Group | More Preferred Synonymous Groups |
| --- | --- | --- |
| Ala | Gly, Thr, Pro, Ala, Ser | Gly, Ala |
| Arg | Asn, Lys, Gln, Arg, His | Arg, Lys, His |
| Asn | Glu, Asn, Asp, Gln | Asn, Gln |
| Asp | Glu, Asn, Asp, Gln | Asp, Glu |
| Cys | Ser, Thr, Cys | Cys |
| Gln | Glu, Asn, Asp, Gln | Asn, Gln |
| Glu | Glu, Asn, Asp, Gln | Asp, Glu |
| Gly | Ala, Thr, Pro, Ser, Gly | Gly, Ala |
| His | Asn, Lys, Gln, Arg, His | Arg, Lys, His |
| Ile | Phe, Ile, Val, Leu, Met | Ile, Val, Leu, Met |
| Leu | Phe, Ile, Val, Leu, Met | Ile, Val, Leu, Met |
| Lys | Asn, Lys, Gln, Arg, His | Arg, Lys, His |
| Met | Phe, Ile, Val, Leu, Met | Ile, Val, Leu, Met |
| Phe | Trp, Phe, Tyr | Tyr, Phe |
| Pro | Gly, Ala, Ser, Thr, Pro | Pro |
| Ser | Gly, Ala, Ser, Thr, Pro | Thr, Ser |
| Thr | Gly, Ala, Ser, Thr, Pro | Thr, Ser |
| Trp | Trp, Phe, Tyr | Trp |
| Tyr | Trp, Phe, Tyr | Phe, Tyr |
| Val | Met, Phe, Ile, Leu, Val | Met, Ile, Val, Leu |

TABLE II

| Amino Acid | Synonymous Group |
| --- | --- |
| Ala | D-Ala, Gly, Aib, B-Ala, Acp, L-Cys, D-Cys |
| Arg | D-Arg, Lys, D-Lys, homo-Arg, D-homo-Arg, Met, Ile, D-.Met, D-Ile, Orn, D-Orn |
| Asn | D-Asn, Asp, D-Asp, Glu, D-Glu, Gln, D-Gln |
| Asp | D-Asp, D-Asn, Asn, Glu, D-Glu, Gln, D-Gln |
| Cys | D-Cys, S—Me-Cys, Met, D-Met, Thr, D-Thr |
| Gln | D-Gln, Asn, D-Asn, Glu, D-Glu, Asp, D-Asp |
| Glu | D-Glu, D-Asp, Asp, Asn, D-Asn, Gln, D-Gln |
| Gly | Ala, D-Ala, Pro, D-Pro, Aib, .beta.-Ala, Acp |

TABLE II-continued

| Amino Acid | Synonymous Group |
|---|---|
| Ile | D-Ile, Val, D-Val, AdaA, AdaG, Leu, D-Leu, Met, D-Met |
| Leu | D-Leu, Val, D-Val, AdaA, AdaG, Leu, D-Leu, Met, D-Met |
| Lys | D-Lys, Arg, D-Arg, homo-Arg, D-homo-Arg, Met, D-Met, Ile, D-Ile, Orn, D-Orn |
| Met | D-Met, S—Me-Cys, Ile, D-Ile, Leu, D-Leu, Val, D-Val |
| Phe | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa |
| Pro | D-Pro, L-I-thioazolidine-4-carboxylic acid, D-or L-1-oxazolidine-4-carboxylic acid |
| Ser | D-Ser, Thr, D-Thr, allo-Thr, Met, D-Met, Met(O), D-Met(O), L-Cys, D-Cys |
| Thr | D-Thr, Ser, D-Ser, allo-Thr, Met, D-Met, Met(O), D-Met(O), Val, D-Val |
| Tyr | D-Tyr, Phe, D-Phe, L-Dopa, His, D-His |
| Val | D-Val, Leu, D-Leu, Ile, D-Ile, Met, D-Met, AdaA, AdaG |

REFERENCES

Ajuebor M N et al., Br J Pharmacol, 125: 319-326, 1998.
Alexander J M et al., Cell, 111: 343-356, 2002.
Ali S et al., Biochem J, 358: 737-745, 2001.
Baggiolini M et al., Annu Rev Immunol, 15: 675-705, 1997.
Baggiolini M, J Intern Med, 250: 91-104, 2001.
Beall C J et al., Biochem J, 313: 633-640, 1996.
Beck C G et al., J Biol Chem, 276: 43270-43276, 2001.
Berhkout T A et al., J Biol Chem, 272: 16404-16413, 1997.
Blaszczyk J et al., Biochemistry, 39:14075-14081, 2000.
Brown A et al., J Pept Sci, 2: 40-46, 1996.
Chen E S et al., Am J Respir Cell Mol Biol; 24: 545-555, 2001.
Chakravarty L et al., J Biol Chem, 273: 29641-29647, 1998.
Cleland J L et al., Curr Opin Biotechnol, 12: 212-219, 2001.
Dawson J, Expert Opin Ther Targets, 7: 35-48, 2003.
Douglas M S et al., Immunology, 92: 512-518, 1997.
Dougherty D A, Curr Opin Chem Biol, 4: 645-652, 2000.
Egashira K et al., FASEB J, 14: 1974-1978, 2000.
Egashira K et al., Circ Res, 90: 1167-1172, 2002.
Eghtesad M et al., Immunology, 102: 157-164, 2001.
Fernandez E J and Lolis E, Annu Rev Pharmacol Toxicol, 42: 469-499, 2002.
Garrigue J L et al., Contact Dermatitis, 30: 231-237, 1994.
Godessart N and Kunkel S L, Curr Opin Immunol, 13: 670-675, 2001.
Golebiowski A et al., Curr Opin Drug Discov Devel, 4: 428-34, 2001.
Gong J and Clark-Lewis I, J Exp Med, 181: 631-640, 1995.
Gonzalo J A et al., J Exp Med, 188: 157-167, 1998.
Gosling J et al., J Clin Invest, 103: 773-778, 1999.
Gu L et al., Chem Immunol, 72: 7-29, 1999.
Gu L et al., Nature, 404: 407-411, 2000.
Handel T M et al., Biochemistry, 35: 6569-6584, 1996.
Hemmerich S et al., Biochemistry, 38: 13013-13025, 1999.
Hogaboam C M et al., J Immunol, 163: 2193-201, 1999.
Hoogewerf A J et al., Biochemistry, 36: 13570-13578, 1997.
Hruby V J and Balse P M, Curr Med Chem, 7: 945-970, 2000.
Huang D R et al., J Exp Med, 193: 713-726, 2001.
Hughes A L and Yeager M, Immunogenetics, 49: 115-124, 1999.
Ikeda Y et al., Am J Physiol Heart Circ Physiol, 283: H2021-2028, 2002.
Kaji M et al., J Biochem, 129: 577-583, 2001.
Kane J F, Curr Opin Biotechnol, 6: 494-500, 1995.
Kuschert G et al., Biochemistry, 38: 12959-12968, 1999.
Loetscher P and Clark-Lewis I, J Leukoc Biol, 69: 881-884, 2001.
Lortat-Jacob H et al, Proc Natl Acad Sci USA, 99: 1229-1234, 2002.
Lu B et al., J Exp Med, 187: 601-608, 1998.
Lubkowski J et al., Nat Struct Biol, 4: 64-69, 1997.
Luo B and Prestwich G D, Exp Opin Ther Patents, 11: 1395-1410, 2001.
Luster A D and Rothenberg M E, J Leukoc Biol, 62: 620-33, 1997.
Madtes D K et al., Am J Respir Cell Mol Biol, 20: 924-934, 1999.
Makrides S C, Protein Expr Purif, 17: 183-202, 1999.
Menten P et al., Eur Cytokine Netw, 12: 554-560, 2001.
Mayer M R and Stone M J, J Biol Chem, 276: 13911-13916, 2001.
McQuibban G A et al., Blood, 100: 1160-1167, 2002.
Mirzadegan T et al., J Biol Chem, 275: 25562-25571, 2000.
Mizumoto N et al., Immunobiology, 204: 477-493, 2001.
Murphy L R et al., Protein Eng, 13: 149-152, 2000.
Nakajima H et al., J Leukoc Biol, 70: 374-380, 2001.
Paavola C D et al., J Biol Chem, 273: 33157-33165, 1998.
Patel D et al., Clin Immunol, 99: 43-52, 2001.
Pillai O and Panchagnula R, Cur Opin Chem Biol, 5: 447-451, 2001.
Proost P et al., J Leukoc Biol, 59: 67-74, 1996.
Proudfoot A, et al. J Biol Chem, 276: 10620-10626, 2001.
Reckless J and Grainger D J, Biochem J, 340: 803-811, 1999.
Rhodes A et al., FEBS Lett, 506: 85-90, 2001.
Rutledge B J et al., J Immunol, 155: 4838-4843, 1995.
Rogov S I and Nekrasov A N, Protein Eng, 14: 459-463, 2001.
Salcedo R et al., Blood, 96: 34-40, 2000.
Sawyer T K, in "Structure Based Drug Design", edited by Veerapandian P, Marcel Dekker Inc., pg. 557-663, 1997.
Seet B T et al., Proc Natl Acad Sci USA, 98: 9008-9013, 2001.
Steitz S A et al., FEBS Lett, 430: 158-164, 1998.
Villain M et al., Chem Biol, 8: 673-9, 2001.
Zhang Y and Rollins B J, Mol Cell Biol, 15: 4851-5, 1995.
Zhang Y et al., Methods 10: 93-103, 1996.

The invention claimed is:

1. An isolated MCP protein comprising:
   a) amino acid substitutions at positions 18 and 19, as numbered on the sequence of human mature MCP-1, said human mature MCP-1 corresponding to amino acids 24-99 of SEQ ID NO: 1, wherein amino acids at positions 18 and 19 are substituted with alanine, glycine, serine, threonine, proline, aspartic acid, asparagine, glutamic acid or glutamine and wherein said MCP protein antagonizes an activity of unaltered MCP proteins; or
   b) amino acid substitutions at positions 18 and 19 and amino acid substitutions at one or more amino acid positions numbered 24, 44, 49, 58, 66 and 75, as numbered on the sequence of human mature MCP-1, said human mature MCP-1 corresponding to amino acids 24-99 of SEQ ID NO: 1, wherein amino acids at positions 18 and 19 are substituted with alanine, glycine, serine, threonine, proline, aspartic acid, asparagine, glutamic acid or glutamine and wherein said MCP protein antagonizes an activity of unaltered MCP proteins.

2. The isolated MCP protein according to claim 1, wherein said MCP protein comprises amino acid substitutions at positions 18 and 19 and amino acid substitutions at one or more amino acid positions numbered 24, 44, 49, 58, 66 and 75, as numbered on the sequence of human mature MCP-1, said human mature MCP-1 corresponding to amino acids 24-99 of SEQ ID NO: 1, wherein amino acids at positions 18 and 19 are substituted with alanine, glycine, serine, threonine, proline, aspartic acid, asparagine, glutamic acid or glutamine and wherein said MCP protein antagonizes an activity of unaltered MCP proteins.

3. The isolated MCP protein according to claim 2, wherein said one or more amino acid positions are substituted with alanine, glycine, serine, threonine, proline, aspartic acid, asparagine, glutamic acid or glutamine.

4. The isolated MCP protein according to claim 1, wherein said MCP protein comprises amino acid substitutions at positions 18 and 19, as numbered on the sequence of human mature MCP-1, said human mature MCP-1 corresponding to amino acids 24-99 of SEQ ID NO: 1, wherein amino acids at positions 18 and 19 are substituted with alanine.

5. The isolated MCP protein according to claim 1, in which one amino acid residue has been added, deleted, or substituted without interfering with the antagonistic activity of said MCP protein with respect to unaltered MCP proteins.

6. The isolated MCP protein according to claim 1, further comprising a heterologous amino acid sequence.

7. The isolated MCP protein according to claim 1, wherein said MCP protein is human MCP-1, human MCP-2, human MCP-3, human MCP-4, or human Eotaxin.

8. The isolated MCP protein according to claim 1, comprising the sequence of SEQ ID NO: 3.

9. The isolated MCP protein according to claim 1, further comprising a molecule chosen from radioactive labels, biotin, fluorescent labels, cytotoxic agents, or drug delivery proteins.

10. The isolated MCP protein according to claim 6, wherein the heterologous amino acid sequence is selected from: extracellular domains of membrane-bound protein, immunoglobulin constant regions, multimerization domains, extracellular proteins, signal peptide-containing proteins or export signal-containing proteins.

11. The isolated MCP protein according to claim 1, wherein said activity is the recruitment of leukocytes.

12. The isolated MCP protein according to claim 2, wherein said activity is the recruitment of leukocytes.

13. The isolated MCP protein according to claim 4, wherein said activity is the recruitment of leukocytes.

14. An isolated nucleic acid encoding a MCP protein comprising:
   a) amino acid substitutions at positions 18 and 19, as numbered on the sequence of human mature MCP-1, said human mature MCP-1 corresponding to amino acids 24-99 of SEQ ID NO: 1, wherein amino acids at positions 18 and 19 are substituted with alanine, glycine, serine, threonine, proline, aspartic acid, asparagine, glutamic acid or glutamine and wherein said MCP protein antagonizes an activity of unaltered MCP proteins; or
   b) amino acid substitutions at positions 18 and 19 and amino acid substitutions at one or more amino acid positions numbered 24, 44, 49, 58, 66 and 75, as numbered on the sequence of human mature MCP-1, said human mature MCP-1 corresponding to amino acids 24 -99 of SEQ ID NO: 1, wherein amino acids at positions 18 and 19 are substituted with alanine, glycine. serine, threonine, proline, aspartic acid, asparagine, glutamic acid or glutamine and wherein said MCP protein antagonizes an activity of unaltered MCP proteins.

15. An expression vector comprising a nucleic acid encoding a MCP protein comprising:
   a) amino acid substitutions at positions 18 and 19, as numbered on the sequence of human mature MCP-1, said human mature MCP-1 corresponding to amino acids 24 -99 of SEQ ID NO: 1, wherein amino acids at positions 18 and 19 are substituted with alanine, glycine, serine, threonine, proline, aspartic acid, asparagine, glutamic acid or glutamine and wherein said MCP protein antagonizes an activity of unaltered MCP proteins; or
   b) amino acid substitutions at positions 18 and 19 and amino acid substitutions at one or more amino acid positions numbered 24, 44, 49, 58, 66 and 75, as numbered on the sequence of human mature MCP-1, said human mature MCP-1 corresponding to amino acids 24 -99 of SEQ ID NO: 1, wherein amino acids at positions 18 and 19 are substituted with alanine, glycine, serine, threonine, proline, aspartic acid, asparagine, glutamic acid or glutamine and wherein said MCP protein antagonizes an activity of unaltered MCP proteins.

16. An isolated host cell transformed with an expression vector comprising a nucleic acid encoding a MCP protein comprising:
   a) amino acid substitutions at positions 18 and 19, as numbered on the sequence of human mature MCP- 1, said human mature MCP- 1 corresponding to amino acids 24 -99 of SEQ ID NO: 1, wherein amino acids at positions 18 and 19 are substituted with alanine, glycine, serine, threonine, proline, aspartic acid, asparagine, glutamic acid or glutamine and wherein said MCP protein antagonizes an activity of unaltered MCP proteins; or
   b) amino acid substitutions at positions 18 and 19 and amino acid substitutions at one or more amino acid positions numbered 24, 44, 49, 58, 66 and 75, as numbered on the sequence of human mature MCP-1, said human mature MCP-1 corresponding to amino acids 24 -99 of SEQ ID NO: 1, wherein amino acids at positions 18 and 19 are substituted with alanine, glycine, serine, threonine, proline, aspartic acid, asparagine, glutamic acid or glutamine and wherein said MCP protein antagonizes an activity of unaltered MCP proteins.

17. A process of preparing a MCP antagonist comprising culturing a host cell transformed with an expression vector comprising a nucleic acid encoding a MCP protein comprising:
   a) amino acid substitutions at positions 18 and 19, as numbered on the sequence of human mature MCP-1, said human mature MCP-1 corresponding to amino acids 24 -99 of SEQ ID NO: 1, wherein amino acids at positions 18 and 19 are substituted with alanine, glycine, serine, threonine, proline, aspartic acid, asparagine, glutamic acid or glutamine and wherein said MCP protein antagonizes an activity of unaltered MCP proteins; or
   b) amino acid substitutions at positions 18 and 19 and amino acid substitutions at one or more amino acid positions numbered 24, 44, 49, 58, 66 and 75, as numbered on the sequence of human mature MCP-1, said human mature MCP-1 corresponding to amino acids 24 -99 of SEQ ID NO: 1, wherein amino acids at positions 18 and 19 are substituted with alanine, glycine, serine, threonine, proline, aspartic acid, asparagine, glutamic acid or glutamine and wherein said MCP protein antagonizes an activity of unaltered MCP proteins.

18. A composition comprising a carrier and a MCP protein comprising:
   a) amino acid substitutions at positions 18 and 19, as numbered on the sequence of human mature MCP-1, said human mature MCP-1 corresponding to amino acids 24 -99 of SEQ ID NO: 1, wherein amino acids at positions 18 and 19 are substituted with alanine, glycine, serine, threonine, proline, aspartic acid, asparagine, glutamic acid or glutamine and wherein said MCP protein antagonizes an activity of unaltered MCP proteins; or
   b) amino acid substitutions at positions 18 and 19 and amino acid substitutions at one or more amino acid positions numbered 24, 44, 49, 58, 66 and 75, as numbered on the sequence of human mature MCP-1, said human mature MCP-1 corresponding to amino acids 24 -99 of SEQ ID NO: 1, wherein amino acids at positions 18 and 19 are substituted with alanine, glycine, serine, threonine, proline, aspartic acid, asparagine, glutamic acid or glutamine and wherein said MCP protein antagonizes an activity of unaltered MCP proteins.

19. The composition according to claim 18, wherein said MCP protein comprises amino acid substitutions at positions 18 and 19 and amino acid substitutions at one or more amino acid positions numbered 24, 44, 49, 58, 66 and 75, as numbered on the sequence of human mature MCP-1, said human mature MCP-1 corresponding to amino acids 24 -99 of SEQ ID NO: 1, wherein amino acids at positions 18 and 19 are substituted with alanine, glycine, serine, threonine, proline, aspartic acid, asparagine, glutamic acid or glutamine and wherein said MCP protein antagonizes an activity of unaltered MCP proteins.

20. The composition according to claim 19, wherein said MCP protein comprises amino acid substitutions at positions 18 and 19, as numbered on the sequence of human mature MCP-1, said human mature MCP-1 corresponding to amino acids 24 -99 of SEQ ID NO: 1, wherein amino acids at positions 18 and 19 are substituted with alanine.

21. The composition according to claim 19, wherein said MCP protein comprises amino acid substitutions at positions 18 and 19, as numbered on the sequence of human mature MCP-1, said human mature MCP-1 corresponding to amino acids 24 -99 of SEQ ID NO: 1, wherein amino acids at positions 18 and 19 are substituted with alanine, glycine, serine, threonine, proline, aspartic acid, asparagine, glutamic acid or glutamine.

22. The composition according to claim 18, wherein said MCP protein further comprises one amino acid residue that has been added, deleted, or substituted without interfering with the antagonistic activity of said MCP protein.

23. The composition according to claim 18, wherein said MCP protein further comprises a heterologous amino acid sequence.

24. The composition according to claim 18, wherein said MCP protein is human MCP-1, human MCP-2, human MCP-3, human MCP-4, or human Eotaxin.

25. The composition according to claim 18, wherein said MCP protein comprises SEQ ID NO: 3.

26. The composition according to claim 18, wherein said MCP protein further comprises a molecule chosen from radioactive labels, biotin, fluorescent labels, cytotoxic agents, or drug delivery proteins.

27. The composition according to claim 23, wherein the heterologous amino acid sequence is selected from: extracellular domains of membrane-bound protein, immunoglobulin constant regions, multimerization domains, extracellular proteins, signal peptide-containing proteins or export signal-containing proteins.

28. The composition according to claim 18, wherein said MCP protein has amino acids at positions 18 and 19 substituted with alanine.

* * * * *

UNITED STATES PATENT AND TRADEMARK OFFICE
CERTIFICATE OF CORRECTION

PATENT NO. : 7,425,324 B2  Page 1 of 1
APPLICATION NO. : 10/510658
DATED : September 16, 2008
INVENTOR(S) : Amanda Proudfoot, Maria Kosco-Vilbois and Tracy Handel It is certified that error appears in the above-identified patent and that said Letters Patent is hereby corrected as shown below:

On the Title Page,
Item (73), Assignee, "Laboratoires Serono SA, Coinsins, Vaud (CH)" should read
--Laboratoires Serono SA, Coinsins, Vaud (CH); The Regents of the University of California, Oakland, California--.

Column 14,
Line 2, "*E. coli* i" should read --*E. coli*--.

Column 17,
Line 4, "C57BU6" should read --C57BL/6--.
Line 32, "C57 BU6NCrIBR" should read --C57 BL/6NCrlBR--.

Signed and Sealed this

Sixteenth Day of December, 2008

JON W. DUDAS
*Director of the United States Patent and Trademark Office*

SEQUENCE LISTING

<160> NUMBER OF SEQ ID NOS: 8

<210> SEQ ID NO 1
<211> LENGTH: 99
<212> TYPE: PRT
<213> ORGANISM: Homo sapiens

<400> SEQUENCE: 1

Met Lys Val Ser Ala Ala Leu Leu Cys Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 2
<211> LENGTH: 77
<212> TYPE: PRT
<213> ORGANISM: Artificial sequence
<220> FEATURE:
<223> OTHER INFORMATION: mutant MCP-1 protein

<400> SEQUENCE: 2

Met Gln Pro Asp Ala Ile Asn Ala Pro Val Thr Cys Cys Tyr Asn Phe
1               5                   10                  15

Thr Asn Arg Lys Ile Ser Val Gln Arg Leu Ala Ser Tyr Arg Arg Ile
            20                  25                  30

Thr Ser Ser Lys Cys Pro Lys Glu Ala Val Ile Phe Lys Thr Ile Val
        35                  40                  45

Ala Lys Glu Ile Cys Ala Asp Pro Lys Gln Lys Trp Val Gln Asp Ser
    50                  55                  60

Ile Asp His Leu Asp Lys Gln Thr Gln Thr Pro Lys Thr
65                  70                  75

<210> SEQ ID NO 3
<211> LENGTH: 77
<212> TYPE: PRT
<213> ORGANISM: Artificial sequence
<220> FEATURE:
<223> OTHER INFORMATION: mutant MCP-1 protein

<400> SEQUENCE: 3

Met Gln Pro Asp Ala Ile Asn Ala Pro Val Thr Cys Cys Tyr Asn Phe
1               5                   10                  15

Thr Asn Ala Ala Ile Ser Val Gln Arg Leu Ala Ser Tyr Arg Arg Ile
            20                  25                  30

Thr Ser Ser Lys Cys Pro Lys Glu Ala Val Ile Phe Lys Thr Ile Val
        35                  40                  45

Ala Lys Glu Ile Cys Ala Asp Pro Lys Gln Lys Trp Val Gln Asp Ser
    50                  55                  60

Ile Asp His Leu Asp Lys Gln Thr Gln Thr Pro Lys Thr
65                  70                  75

<210> SEQ ID NO 4
<211> LENGTH: 76
<212> TYPE: PRT
<213> ORGANISM: Homo sapiens

<400> SEQUENCE: 4

```
Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
50                      55                  60

Asp His Leu Asp Lys Gln Thr Gln Thr Pro Lys Thr
65                  70                  75
```

<210> SEQ ID NO 5
<211> LENGTH: 76
<212> TYPE: PRT
<213> ORGANISM: Homo sapiens

<400> SEQUENCE: 5

```
Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
50                      55                  60

Lys His Leu Asp Gln Ile Phe Gln Asn Leu Lys Pro
65                  70                  75
```

<210> SEQ ID NO 6
<211> LENGTH: 76
<212> TYPE: PRT
<213> ORGANISM: Homo sapiens

<400> SEQUENCE: 6

```
Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
            20                  25                  30

Ser Ser His Cys Pro Arg Glu Ala Val Ile Phe Lys Thr Lys Leu Asp
            35                  40                  45

Lys Glu Ile Cys Ala Asp Pro Thr Gln Lys Trp Val Gln Asp Phe Met
50                      55                  60

Lys His Leu Asp Lys Lys Thr Gln Thr Pro Lys Leu
65                  70                  75
```

<210> SEQ ID NO 7
<211> LENGTH: 75
<212> TYPE: PRT
<213> ORGANISM: Homo sapiens

<400> SEQUENCE: 7

```
Gln Pro Asp Ala Leu Asn Val Pro Ser Thr Cys Cys Phe Thr Phe Ser
1               5                   10                  15

Ser Lys Lys Ile Ser Leu Gln Arg Leu Lys Ser Tyr Val Ile Thr Thr
            20                  25                  30

Ser Arg Cys Pro Gln Lys Ala Val Ile Phe Arg Thr Lys Leu Gly Lys
            35                  40                  45

Glu Ile Cys Ala Asp Pro Lys Glu Lys Trp Val Gln Asn Tyr Met Lys
```

```
                  50                55                60
His Leu Gly Arg Lys Ala His Thr Leu Lys Thr
65                  70                  75

<210> SEQ ID NO 8
<211> LENGTH: 74
<212> TYPE: PRT
<213> ORGANISM: Homo sapiens

<400> SEQUENCE: 8

Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
                20                  25                  30

Lys Cys Pro Gln Lys Ala Val Ile Phe Lys Thr Lys Leu Ala Lys Glu
            35                  40                  45

Ile Cys Ala Asp Pro Lys Lys Lys Trp Val Gln Asp Ser Met Lys Tyr
        50                  55                  60

Leu Asp Gln Lys Ser Pro Thr Pro Lys Pro
65                  70
```